(12) United States Patent
Ahmad et al.

(10) Patent No.: US 10,782,284 B1
(45) Date of Patent: Sep. 22, 2020

(54) BREATH ANALYSIS SYSTEM

(71) Applicant: Invoy Holdings, LLC, Aliso Viejo, CA (US)

(72) Inventors: Lubna Ahmad, Chandler, AZ (US);
Zachary Smith, Phoenix, AZ (US);
Salman Ahmad, Chandler, AZ (US);
Connie Kim, Garden Grove, CA (US);
Ayman Luqman, Dallas, TX (US)

(73) Assignee: Invoy Holdings Inc., Irvine, CA (US)

( * ) Notice: Subject to any disclaimer, the term of this patent is extended or adjusted under 35 U.S.C. 154(b) by 0 days.

(21) Appl. No.: 16/590,046

(22) Filed: Oct. 1, 2019

Related U.S. Application Data

(60) Provisional application No. 62/831,017, filed on Apr. 8, 2019, provisional application No. 62/773,045, filed on Nov. 29, 2018.

(51) Int. Cl.
| | | |
|---|---|---|
| *G01N 33/497* | (2006.01) | |
| *G01N 21/03* | (2006.01) | |
| *G01N 21/05* | (2006.01) | |
| *G01N 21/31* | (2006.01) | |

(52) U.S. Cl.
CPC ......... *G01N 33/497* (2013.01); *G01N 21/031* (2013.01); *G01N 21/0303* (2013.01); *G01N 21/05* (2013.01); *G01N 21/314* (2013.01); *G01N 2033/4975* (2013.01); *G01N 2201/0627* (2013.01)

(58) Field of Classification Search
CPC ....... A61B 5/082; A61B 5/7271; A61B 5/097; A61B 2562/08; A61B 2560/0487; G01N 33/497; G01N 21/314; G01N 21/031; G01N 21/05; G01N 2201/0627
See application file for complete search history.

(56) References Cited

U.S. PATENT DOCUMENTS

| | | |
|---|---|---|
| 5,071,769 A | 12/1991 | Kundu et al. |
| 5,818,580 A | 10/1998 | Murnick |
| 5,834,626 A | 11/1998 | De Castro et al. |
| 6,219,567 B1 | 4/2001 | Eggers et al. |
| 9,689,864 B2 | 6/2017 | Ahmad et al. |
| 10,226,201 B2 | 3/2019 | Ahmad et al. |
| 2004/0017570 A1 | 1/2004 | Parikh et al. |
| 2005/0083527 A1 | 4/2005 | Flaherty et al. |
| 2006/0145078 A1* | 7/2006 | Russell .............. A61B 5/083 250/343 |
| 2008/0056946 A1 | 3/2008 | Ahmad |
| 2009/0290161 A1 | 11/2009 | Atkin et al. |

(Continued)

*Primary Examiner* — David Z Huang
(74) *Attorney, Agent, or Firm* — Knobbe, Martens, Olson & Bear, LLP

(57) ABSTRACT

A breath analyte capture device includes a breath input port into which a user exhales a breath sample, and a cartridge insertion port for receiving a disposable cartridge containing an interactant. During exhalation of a breath sample, at least a portion of the breath sample is routed through the cartridge such that the analyte (such as breath acetone) is captured by the interactant. In some embodiments, the concentration of the analyte in the breath sample is measured by monitoring a chemical reaction that occurs in the disposable cartridge. The chemical reaction may be monitored by illuminating the cartridge at each of multiple light wavelengths while measuring reflected light.

21 Claims, 20 Drawing Sheets

(56) References Cited

U.S. PATENT DOCUMENTS

| | | | |
|---|---|---|---|
| 2014/0376762 A1* | 12/2014 | Lipman | A61B 5/150022 |
| | | | 381/365 |
| 2016/0054294 A1 | 2/2016 | Rihani et al. | |
| 2016/0262657 A1* | 9/2016 | Ahmad | A61B 5/097 |
| 2019/0350495 A1* | 11/2019 | Ahmad | A61B 5/097 |

* cited by examiner

SECTION A-A

BREATH ANALYSIS SYSTEM

PRIORITY CLAIM

This application claims the benefit of U.S. Provisional Appl. Nos. 62/831,017, filed Apr. 8, 2019, and 62/773,045, filed Nov. 29, 2018, the disclosures of which are hereby incorporated by reference.

BACKGROUND

Technical Field

The present invention relates to breath analysis devices for measuring ketones in breath, and more specifically, to devices that can be provided to, and used by, participants in various types of health programs, such as weight loss and fitness programs.

Description of the Related Art

Various types of devices exist for allowing individuals to measure their breath ketone levels. These devices can be provided to participants in various types of health programs to enable the participants—and in some cases their health coaches—to monitor participant progress. For example, breath analysis devices that measure breath acetone levels can be provided to participants in a weight management or fitness program to facilitate daily monitoring of fat metabolism. As another example, breath analysis devices that measure carbon monoxide can be used to monitor progress in a smoking cessation program.

Health programs that rely on breath analysis for progress monitoring are often of limited utility because the breath analysis devices are difficult or inefficient for participants to use. For example, in many cases, the participant has to perform a large number of steps to take a single breath measurement, and the failure to properly perform each step can result in an erroneous measurement or in premature termination of the test. As another example, the processing time needed to analyze the participant's breath sample can be significant (e.g., a minute or more). As yet another example, participants may be required to log significant quantities of data (such as diet non-compliance events), and/or to use two more separate measurement devices to measure different respective physiologic parameters.

These and other factors can dissuade users from participating in the associated programs, and can produce low quality data.

BRIEF DESCRIPTION OF THE DRAWINGS

FIGS. 3A and 3B, illustrates the operation of the cartridge ejection mechanism of the ketone capture device of FIGS. 1 and 2.

FIG. 15A shows a side view; FIG. 15B shows a top view; FIG. 15C shows a cut-away view of a side view; and FIG. 15D shows a bottom view.

DETAILED DESCRIPTION OF THE PREFERRED EMBODIMENTS

Figure 1:
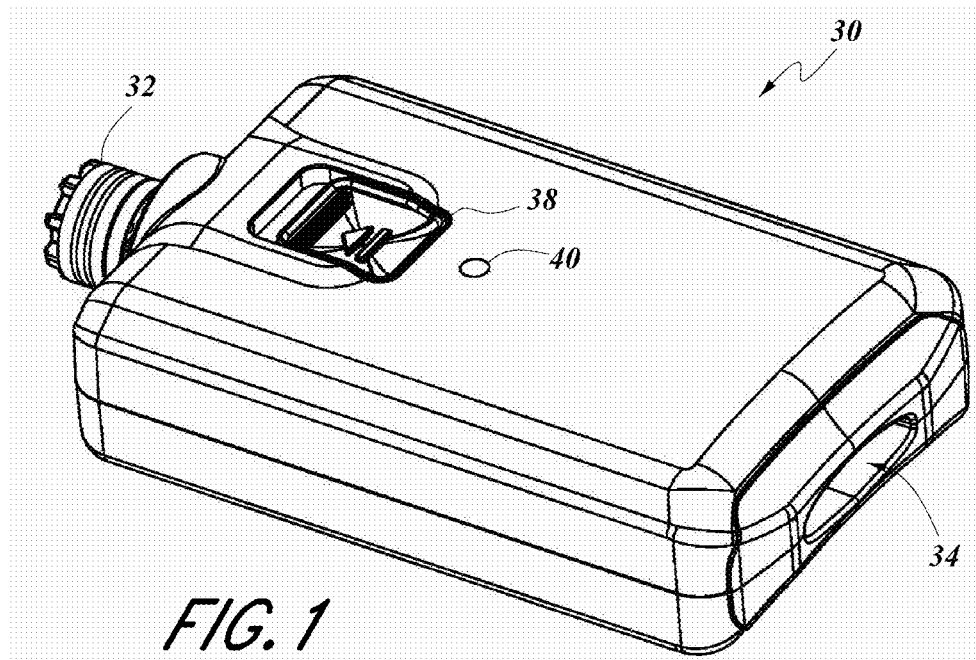
FIG. 1 is a perspective view of a handheld breath ketone capture device according to one embodiment. A disposable cartridge is shown partially inserted into the ketone capture device.
Figure 2:
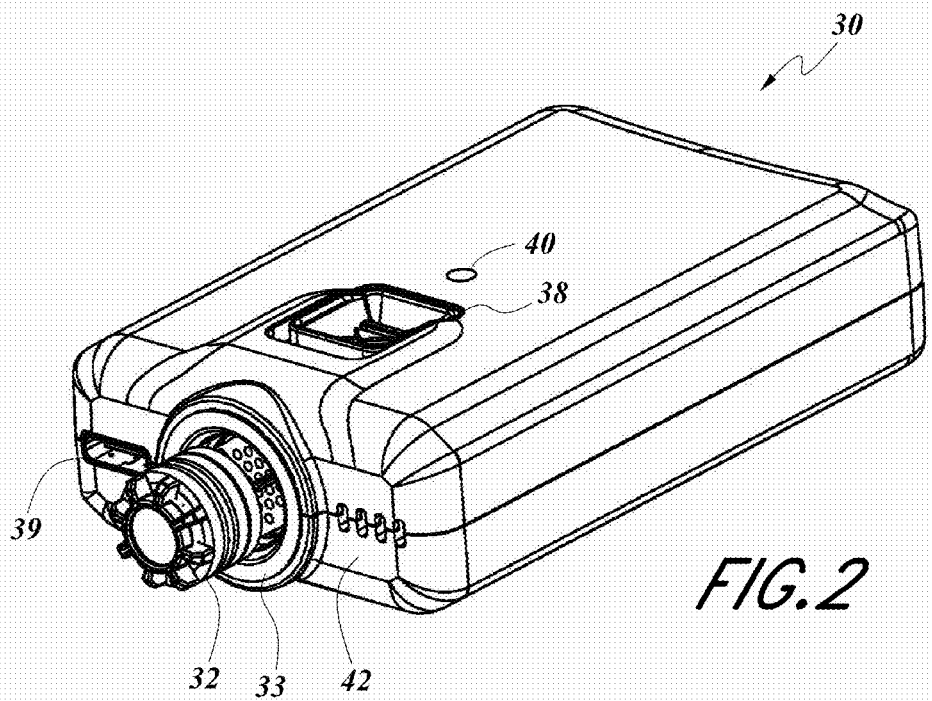
FIG. 2 is another perspective view of the ketone capture device of FIG. 1.

FIGS. 1-7 illustrate embodiments of a handheld breath ketone capture device 30 ("ketone capture device") that uses a disposable sample collection cartridge 32 to capture ketones, such as acetone, in breath samples of users. The ketone capture device 30 has a breath input port 34 into which a user exhales a breath sample. The ketone capture device 30 also includes a cartridge insertion port 36 configured to receive a disposable cartridge 32 containing an interactant material. The cartridge insertion 36 port includes a deformable seal 33 (FIG. 2) that forms an airtight seal with the cartridge when the cartridge 32 is inserted. Different cartridges (containing different interactants) may be provided for measuring different ketones, such as acetone, ammonia, methane, hydrogen, carbon dioxide, ethanol, isoprene, aldehydes, and other volatile organic compound analytes. In addition, some embodiments may support a multi-chamber cartridge in which each chamber includes a different interactant for measuring a different ketone. One embodiment of a cartridge 32 is shown in FIGS. 15-18 and described below.

Figure 3:
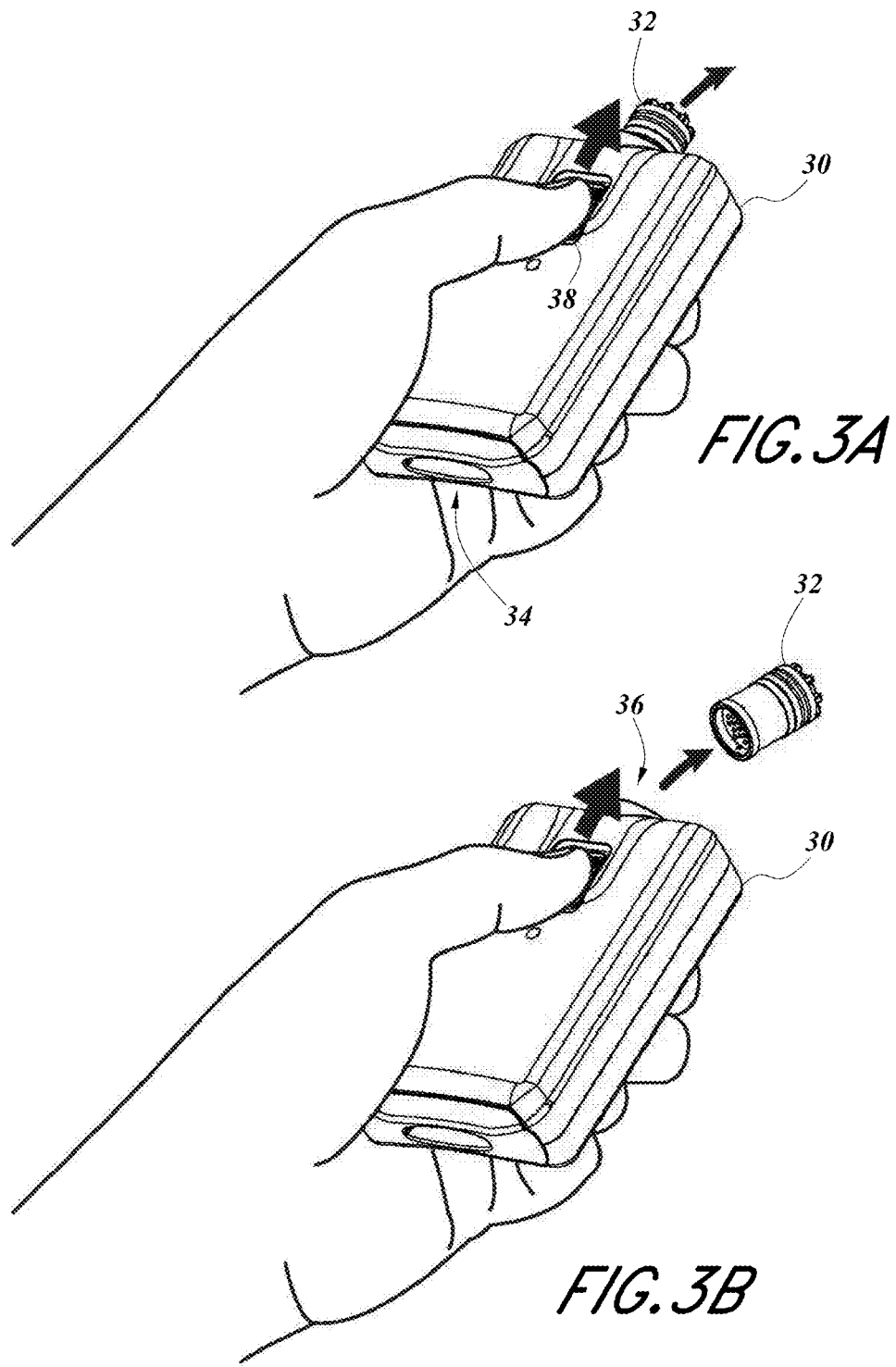
FIG. 3, which includes

To remove the cartridge 32, the user depresses an ejection button 38, which causes the ketone capture device to release and expel the cartridge (as shown in FIG. 3). In one embodiment, the force applied by the user to the ejection button is transmitted via a protrusion or arm (39 in FIGS. 7A and 7B) to the deformable seal 33, causing the seal to release and expel the cartridge 32 without the need for an ejection mechanism within the airtight flow path. As explained below, in some embodiments, a processor of the ketone capture device may disable the ejection button 38 when a test is being performed, to thereby inhibit or prevent a user from prematurely ejecting the cartridge 32.

In the illustrated embodiments, the ketone capture device includes an LED indicator 40 that provides status information to the user. Although not illustrated in the drawings, the LED indicator 40 may be elevated relative to the flat surface of the housing, and/or angled toward the influent end of the device, so that it can easily be viewed by the user during the exhalation process. In addition or alternatively, the LED indicator may be spaced sufficiently from the breath input port 34 (e.g., by at least 2 inches, by at least 3 inches, etc.) so that the user can easily see it. The LED indicator 40 may be replaced with, or supplemented by, various other types of status indicators, such as a display screen that displays textual messages, a tone generator or buzzer 201 (shown in the block diagram of FIG. 12), a haptic device that generates haptic notifications, and/or a speaker that outputs audible voice prompts. The ketone capture device also includes a Bluetooth transceiver (shown as 204 in FIG. 12) that communicates with a mobile application that runs on a smartphone or other wireless communications device of the user. The mobile application preferably displays status information to the user during the breath capture and analysis process, as described below and shown in FIG. 11. As described below, the mobile application is preferably configured to run in the background on the phone when not in active use, and the phone is preferably configured to bring the mobile application to the foreground (or to enable the user to easily do so) in response to the establishment of a Bluetooth connection with the ketone capture device 30. Although Bluetooth (and preferably Bluetooth Low Energy or "BLE") is used in the illustrated embodiments, WIFI or any other wireless standard commonly implemented in phones can be used to provide the wireless link between the ketone capture device and the phone. A USB connector/port 39 is provided for charging the device's rechargeable battery.

To use the ketone capture device 30 in the illustrated embodiments, the user inserts a disposable cartridge 32 into the cartridge insertion port 36, waits for the LED indicator 40 to turn blue (or another color representing a "ready" state), and then exhales a breath sample into the breath input port 34. The user advantageously does not have to turn ON the ketone capture device before or during this process; this is because the ketone capture device operates in a low-power state when not in use, and transitions automatically into a higher power "ready state" in response to the insertion of the cartridge 32. In addition, the user need not bring the mobile application to the foreground on the phone and need not take any additional action to establish a wireless connection between the ketone capture device and the phone at the time of the breath test. Instead, as described below, the ketone capture device automatically establishes a BTE connection with the phone (e.g., in response to cartridge insertion), causing the phone to bring the mobile application (which runs in the background when not in use) to the foreground. Further, although the mobile application provides status information during the process, the user preferably need not interact with the mobile application during this process. These and other aspects of the design simplify the measurement process for users, making the task of taking daily measurements more practical for program participants.

Figure 4:
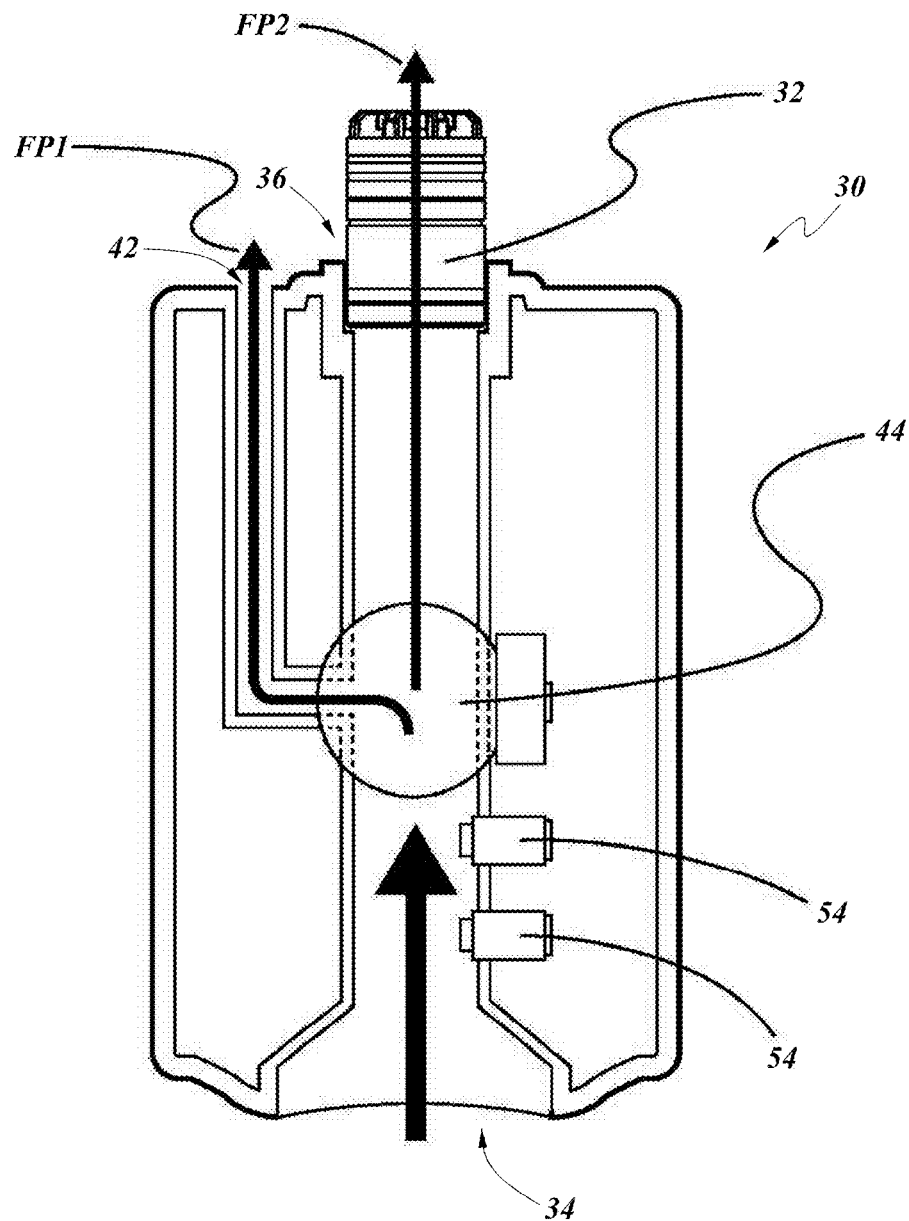
FIG. 4 is a functional drawing showing flow paths, a motor-controlled valve, and sensors included in the embodiment of FIGS. 1-3.
Figure 5:
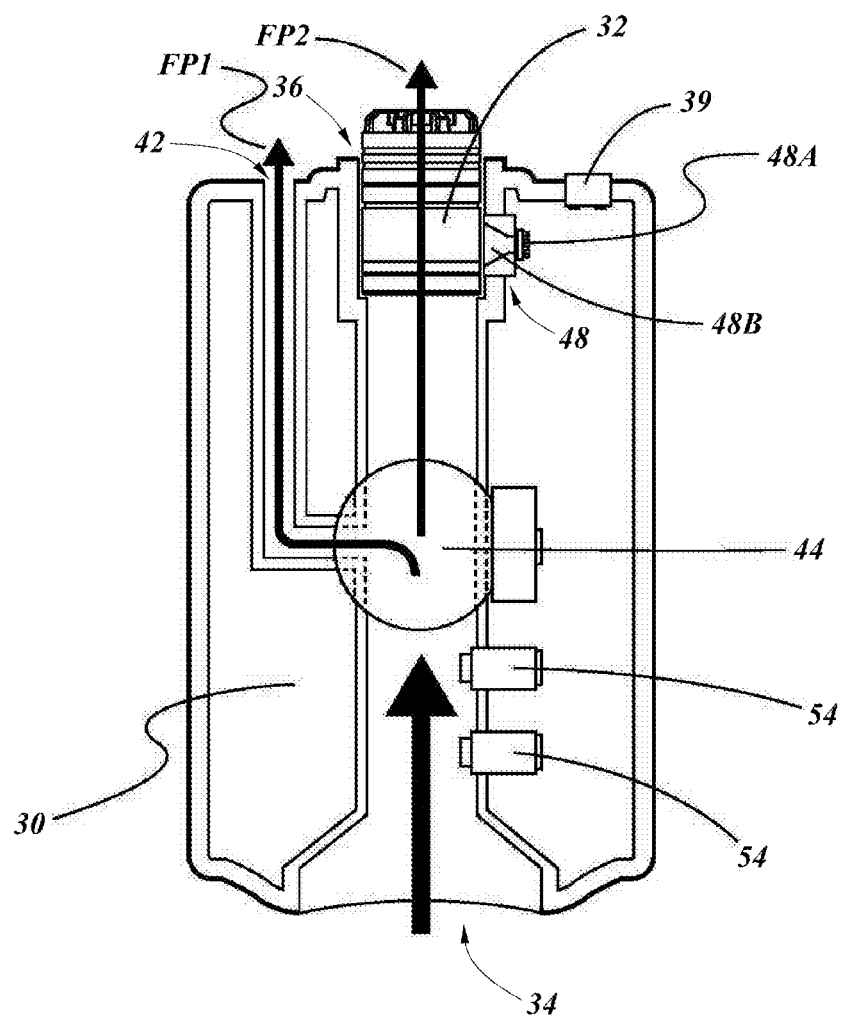
FIG. 5 is a functional diagram illustrating another embodiment in which the ketone capture device includes an optical sensor, such as a LED/photodiode assembly, for analyzing the cartridge after the user exhales through the ketone capture device.
Figure 6:
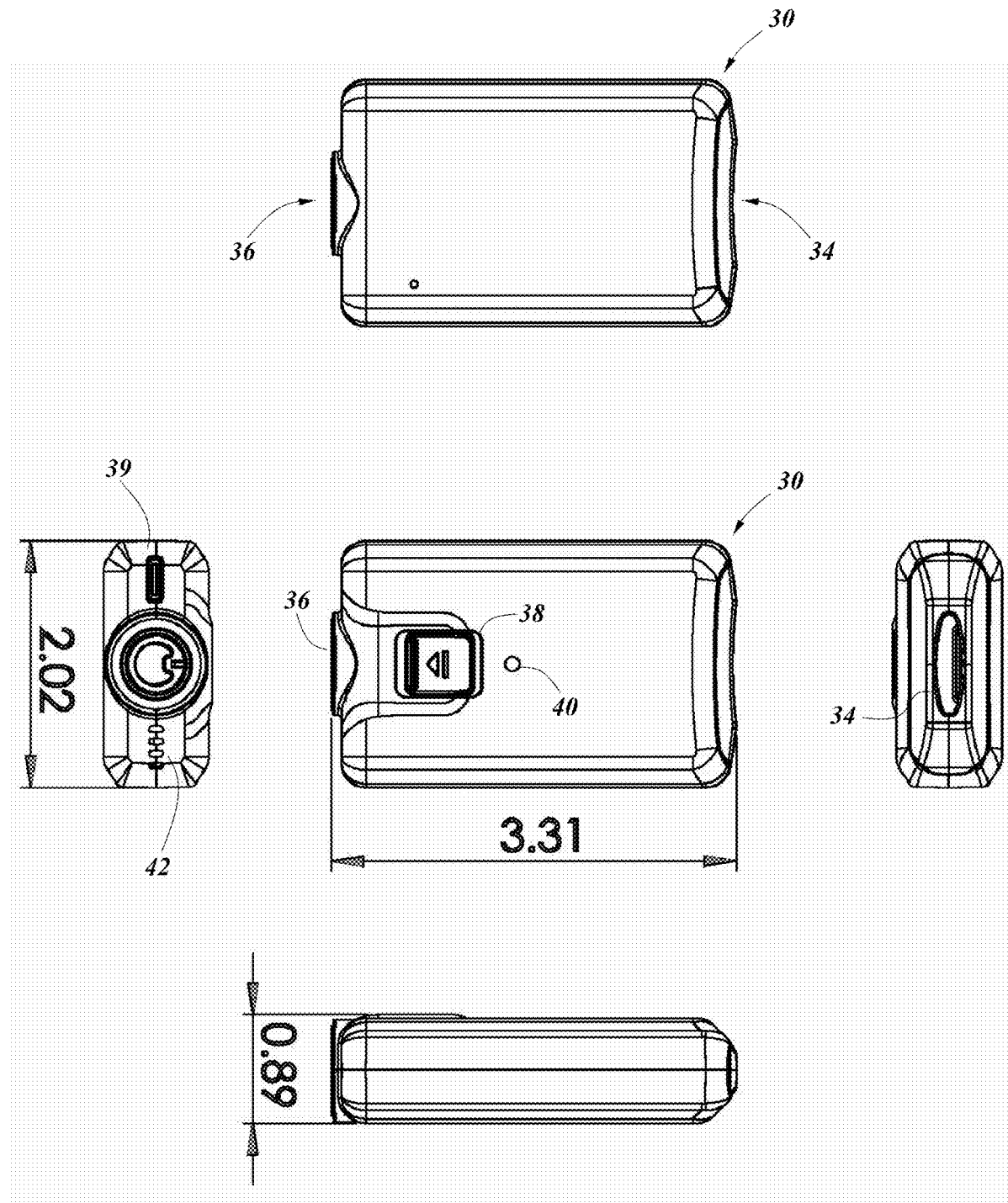
FIG. 6 illustrates dimensions (in inches) of the ketone capture devices of FIGS. 1-5.

During an initial portion of the exhalation process, the breath sample is routed out of a venting port 42 of the device 30 along flow path FP1 (FIGS. 4 and 5), such that the initial portion of the breath sample does not pass through the cartridge 32. Once the user has exhaled for a sufficient period of time (or has exhaled a sufficient volume of breath), a processor-controlled valve 44 (which may be an electromechanical device that includes a motor) is activated to cause some or all of the remaining breath sample to flow along flow path FP2, and thus through the cartridge 32. The portion that passes through the cartridge 32 thus consists mostly or entirely of deep alveolar breath, which is generally more useful for measuring breath ketones. The ketone of interest is absorbed by the interactant material in the cartridge during this process. The drawings in FIGS. 4 and 5 are functional drawings that are not intended to show the actual positions and configurations of the illustrated components. In contrast, FIGS. 1-3, 6 and 7A are drawn to scale and show actual arrangements and configurations of components.

Figure 7A:
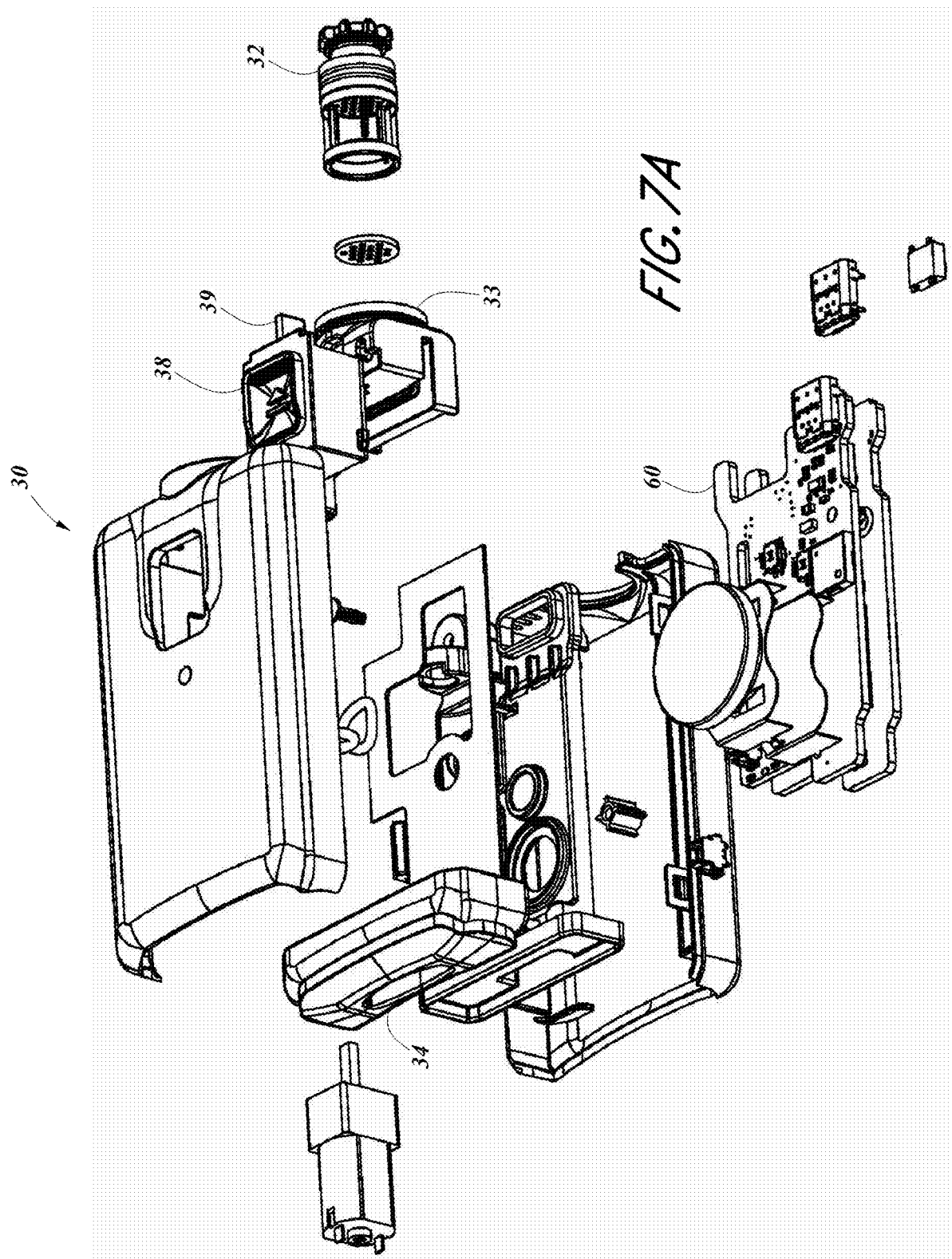
FIGS. 7A and 7B are exploded views showing the primary components of the embodiment of FIGS. 1-4.
Figure 7B:
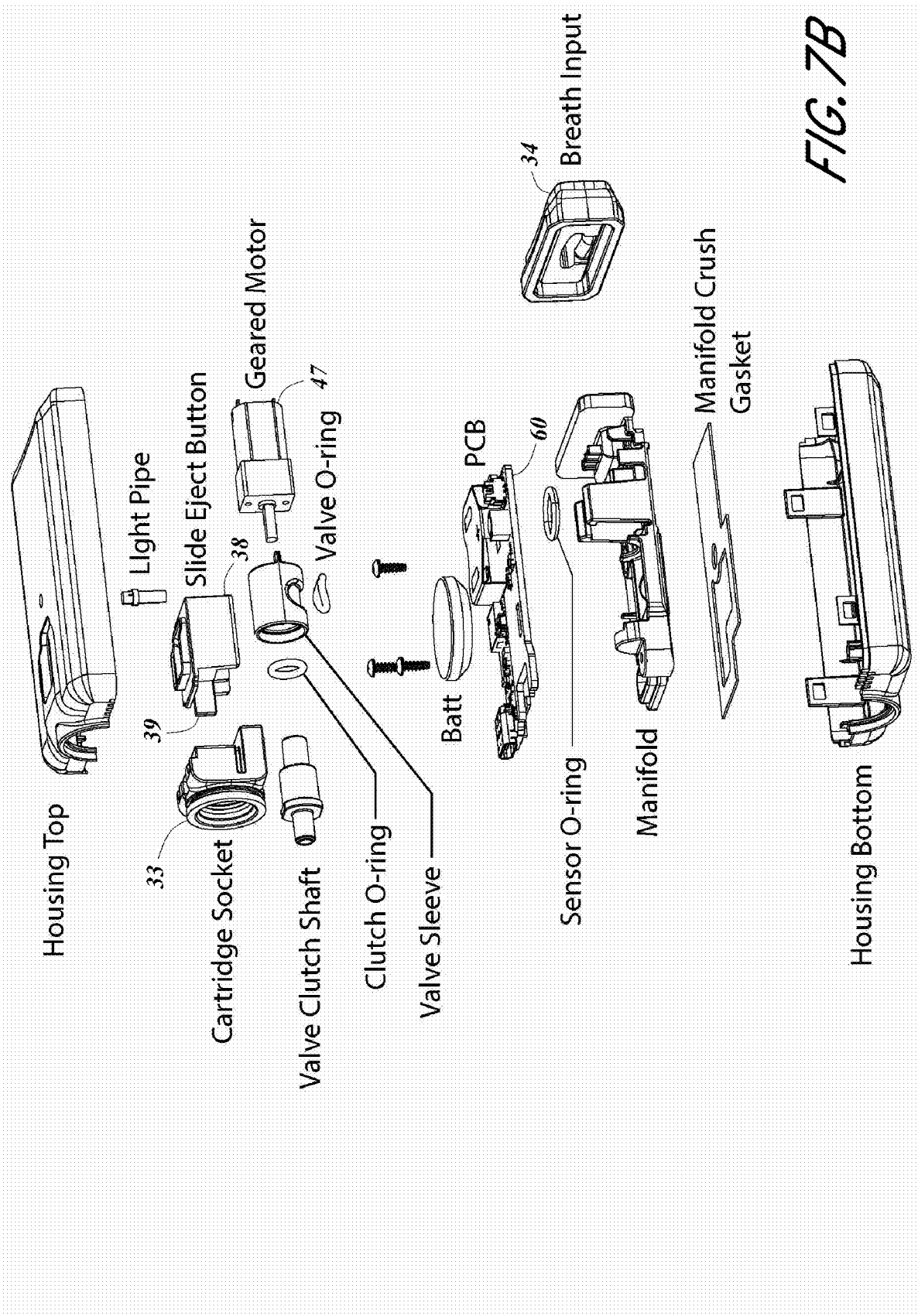

In one embodiment, the processor-controlled valve 44 is a rotary valve driven by a geared CAM motor 47 (FIG. 7B). The rotary valve includes a clutch, allowing the motor 47 to continue to turn once the valve has been switched to its desired position. One benefit of this arrangement is that no feedback is needed regarding the position of the valve. In other embodiments, the valve may be driven by a servo motor. In one embodiment, when the valve is in the open position, breath exhaled into the device 30 is vented through the venting port 42 along FP1, and when the valve is closed, breath exhaled into the device is routed through the cartridge along flow FP2. In some embodiments, when the valve 44 is open, the breath exhaled into the device 30 can exit the device along both FP1 and FP2; however, because of the added flow resistance produced by the cartridge 32, very little or no breath actually exits the device through flow FP2.

Once the user finishes exhaling into the ketone capture device 30, the user either ejects the cartridge 32 and places it in a separate base unit (FIG. 19) for analysis, or else waits for the ketone capture device 30 to analyze the cartridge. Examples of cartridge and base unit designs that may be used are disclosed in U.S. Provisional Appl. No. 62/675,109, filed May 22, 2018, the disclosure of which is hereby incorporated by reference. Embodiments in which the ketone capture device performs its own analysis of the cartridge are referred to herein as "standalone" embodiments. The embodiments in which the user moves the cartridge 32 to a base unit for analysis are referred to herein as "non-standalone" embodiments. In non-standalone embodiments, the mobile application communicates with both the ketone capture device 30 and the base unit via Bluetooth. FIGS. 1-4 and 7 illustrate a non-standalone embodiment, and FIG. 5 illustrates a standalone embodiment. The dimensions shown in FIG. 6 (which are in inches) are applicable to both standalone and non-standalone embodiments, although numerous other sizes and configurations are possible.

The standalone embodiment of FIG. 5 differs from the non-standalone embodiments in two major respects. First, the standalone device 30 includes an optical sensor 48 for measuring a color change, or other optical change, produced by a chemical reaction in the cartridge 32. Second, the cartridge inserts farther into the cartridge insertion port 36 so that the optical sensor 38 aligns with a transparent window of the cartridge 32 when the cartridge is fully inserted. (In one embodiment, which is shown in FIGS. 15-18, the transparent window 412 is positioned at one end of the cartridge 32.) In the preferred embodiment, the optical sensor 48 comprises an LED array 48A that illuminates an interactant chamber of the cartridge through the transparent window, and comprises a photodiode 48B that measures a color or intensity change produced by the chemical reaction in this chamber. In non-standalone embodiments, the LED/photodiode assembly (or other optical sensor 48) is included in the base unit.

Standalone embodiments of the ketone capture device 30 preferably use a "single step reaction" type cartridge 32 in which the chemical reaction in the cartridge occurs in response to the user's breath sample passing through the cartridge. For example, in the case of acetone, the acetone reacts with the interactant in the cartridge 32, causing a color change that can be sensed. The magnitude of this color change is dependent upon the quantity of acetone absorbed by the interactant in the cartridge 32. Single-step reaction cartridges do not require the introduction of a liquid into the cartridge 32 to trigger the chemical reaction. Different interactants can be used to measure different ketones.

Figure 19:
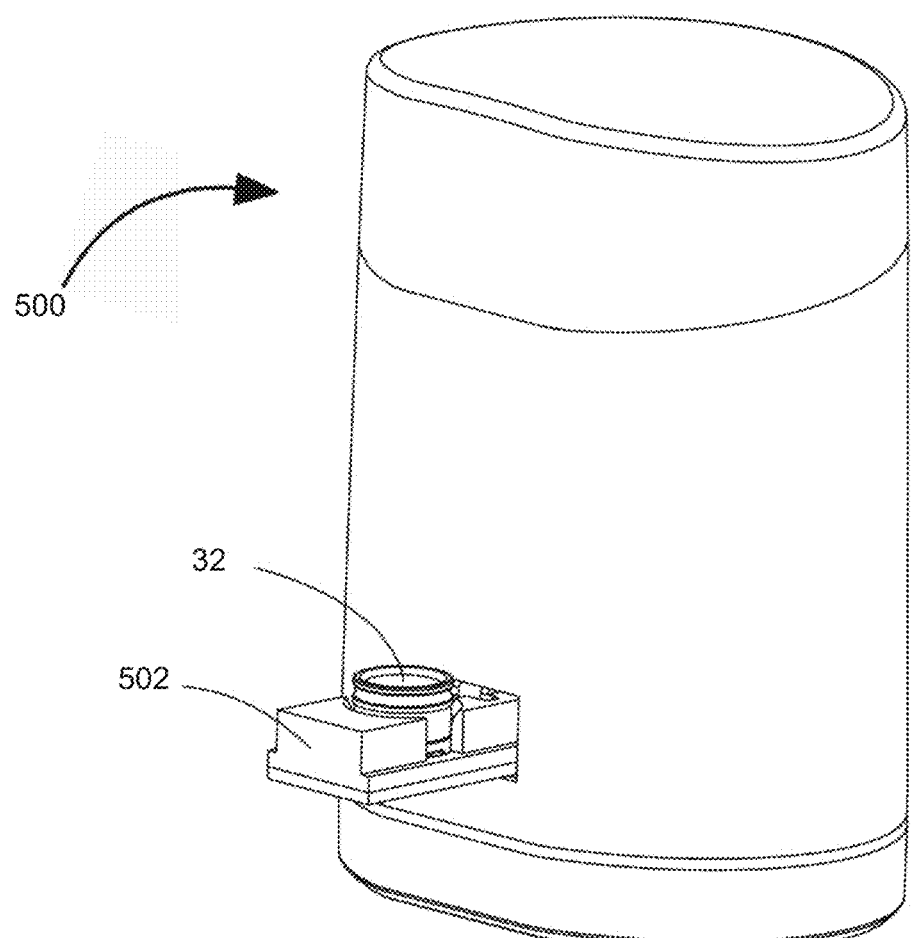
FIG. 19 illustrates one embodiment of a base unit.

Non-standalone embodiments of the ketone capture device preferably use a "two-step reaction" type cartridge 32 that requires the introduction of a liquid developer solution into the cartridge 32 after the breath sample has been passed through the cartridge. The task of dispensing the developer solution into the cartridge 32 is performed by the base unit (FIG. 19). Once dispensed, the developer solution triggers a chemical reaction that produces a color change that is dependent upon the quantity of the ketone being measured. Thus, after dispensing the developer solution into the cartridge 32, the base unit waits a sufficient time for the reaction to occur, measures the color or color change (preferably using an LED/photodiode assembly), and transmits the result to the mobile application.

As shown in FIGS. 4 and 5, both standalone and non-standalone embodiments of the ketone capture device 30 preferably include one or more sensors 54 for measuring one or more characteristics of the breath sample upstream from the valve 44. The sensor(s) 54 preferably include a pressure sensor that is used both to detect the initiation of exhalation and to determine whether the exhalation characteristics are sufficient for a generating a valid ketone measurement. The sensor(s) 54 may also include a temperature sensor that is used to provide additional data for validating the exhalation, as explained below. The temperature sensor may also be used to capture and log body temperature data for health monitoring purposes. Various other types of sensors 54 may be included for measuring other characteristics of the breath sample; for example, the ketone capture device may also include an ethanol (alcohol) sensor, a carbon monoxide sensor for smoking cessation programs, a carbon dioxide sensor for monitoring energy metabolism, and/or a humidity sensor. As discussed below with reference to FIG. 9, the ketone capture device may also be augmented with a pulse oximeter.

Figure 8:
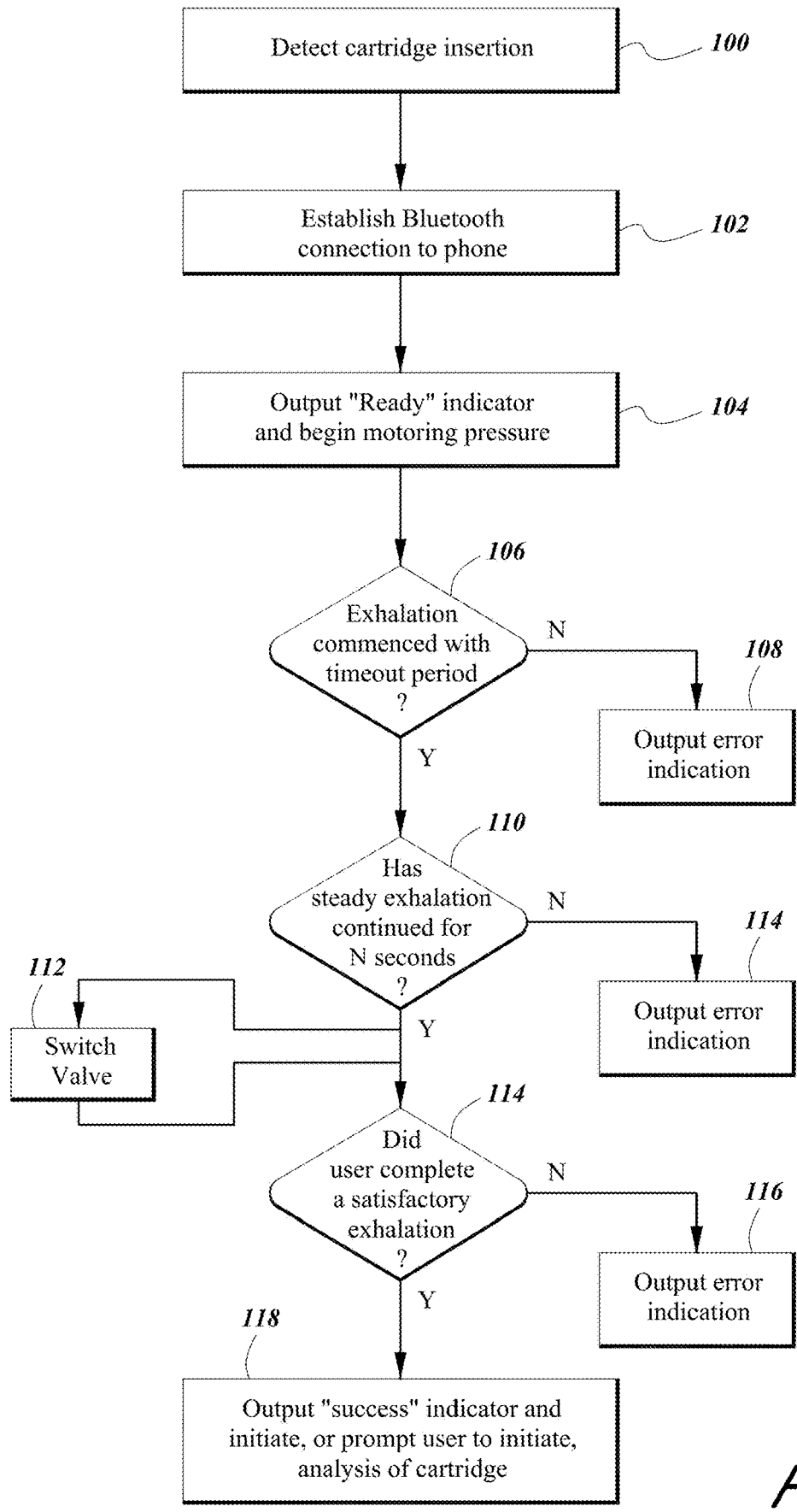
FIG. 8 is a flow chart illustrating the main steps of a processor-controlled process implemented by the ketone capture devices of the preceding figures in connection with an exhalation event.

FIG. 8 illustrates the primary steps of a process performed by the ketone capture device 30 in some embodiments. The illustrated process is performed under the control of firmware executed by the device's processor, and is initiated when a user inserts a disposable cartridge 32. The drawing is applicable to both the non-standalone embodiments (FIGS. 1-4 and 6-7) and the standalone embodiments (FIGS. 5 and 6) of the ketone capture device 30.

In block 100 of FIG. 8, the ketone capture device 30 detects, via a bump switch or other presence sensor (shown in FIG. 12), the insertion of a disposable cartridge 32 into the cartridge insertion port 36. In some embodiments (and especially the standalone embodiments), the processor may disable the ejection button 38 from this point until the process is complete to inhibit the user from prematurely removing the cartridge. (The ejection button may be disabled in a variety of ways, such as by using a solenoid or motor-driven blocking device to block the ejection button from moving, or by using a processor-driven ejection mechanism that generates an electro-mechanical force when activated by a processor.) For example, in standalone embodiments, the ejection button may be disabled until the ketone capture device 30 has finished analyzing the cartridge 32.

Figure 11:
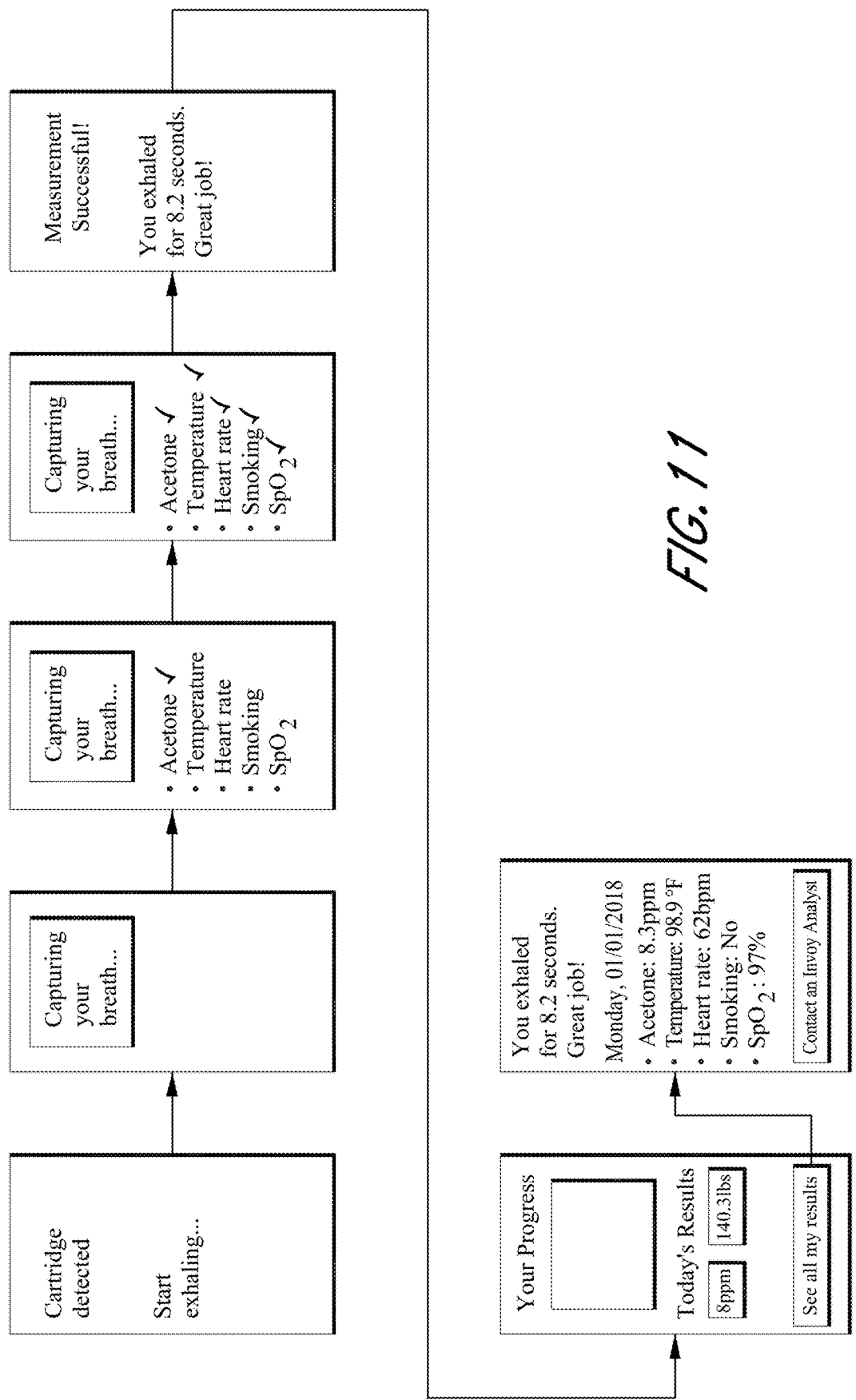
FIG. 11 illustrates example screens or screen content that may be displayed by the mobile application in connection with a breath test.

In block 102, the ketone capture device 30 establishes a Bluetooth connection with the user's phone (or other wireless communication device such as a tablet). As discussed above, once this connection is established, the phone automatically launches (or brings to the forefront) the mobile application and begins to display status information. Example screens that are displayed during the process are illustrated in FIG. 11 and are described below. If the ketone capture device 30 is unable to establish a Bluetooth connection within a selected timeout period, the ketone capture device may output an error indication, such as by turning the LED indicator red or displaying a flashing red indicator. Alternatively, in some embodiments, the ketone capture device 30 may allow the ketone capture process to proceed without a wireless connection to the phone, in which case the ketone capture device may communicate the measurement data to the mobile application when a connection is later established between the ketone capture device and the phone.

In block 104, the ketone capture device 30 outputs a "ready" indicator (such as by turning the LED indicator 40 blue) and begins monitoring pressure with the pressure sensor 54 to detect the initiation of exhalation. (In some embodiments, the ketone capture device 30 additionally or alternatively monitors the temperature along the breath flow path, as described below.) The ready indicator indicates that the user can start exhaling (blowing) into the breath input port 34 of the ketone capture device 30. The ketone capture device may also notify the phone of the ready condition, in which case the mobile application may display a message instructing the user to begin exhalation (see FIG. 11).

In decision block 106 of FIG. 8, the ketone capture device 30 determines, based on the monitored pressure (and/or temperature), whether exhalation has commenced. If exhalation does not commence within a selected timeout period such as 30 seconds, the ketone capture device 30 in block 108 outputs an error indication (e.g., a red or red flashing LED) and terminates the process. At this point the user may restart the process by ejecting and then re-inserting the cartridge 32.

In decision block 110, the process waits until steady state exhalation (e.g., exhalation above a threshold pressure) has continued for N seconds, and then switches the valve to the closed or "flow path 2" position in block 112. The purpose of waiting for N seconds is to cause the exhaled "dead space" air in the user's trachea and lungs to be expelled without passing through the cartridge 32, so that the breath that passes through the cartridge consists essentially or entirely of deep alveolar breath. The time delay N may be a fixed value in the range of 1 to 5 seconds, or more preferably 2 to 4 seconds (e.g., 3 seconds). Alternatively, the value of N may be selected programmatically based on one or more characteristics of the user or one or more characteristics of the exhalation (e.g., the sensed pressure). For example, N may be selected to be proportional to the user's weight or measured lung capacity. The value of N may also be adjusted in real time based on pressure and/or temperature measurements. If steady state exhalation does not continue for N seconds following exhalation commencement, the ketone capture device 30 may output an error indication and terminate the process (block 114).

In decision block 114, the ketone capture device 30 determines whether the user has completed a satisfactory exhalation. In one embodiment, this determination involves monitoring the pressure to ensure that it remains above a selected threshold, such as 7 kPa above standard atmospheric pressure, for a threshold exhalation period following exhalation commencement. (In some embodiments, an upper pressure threshold may also be used, as may be desirable, for example, for discarding exhalations in which the user coughs or sneezes.) The threshold or minimum exhalation period may, for example, be in the range of 5 to 14 seconds, 6 to 12 seconds, or 7 to 11 seconds, and may either be a fixed value or a value selected programmatically based on characteristics of the user and/or exhalation. For example, a minimum exhalation period of 8 seconds, and a target (ideal) exhalation period of 10 seconds, may be used. As explained below, the ketone measurement process may compensate for exhalations that are satisfactory but not ideal. The following are examples of events that may cause a user's exhalation to be unsatisfactory: the user sneezes or coughs during exhalation; the user inhales through the ketone capture device before exhaling; the user inhales mid-breath during the test; the user exhales dynamically in short, irregular breaths; the user does not exhale long enough to generate a useful measurement.

In some embodiments, the ketone capture device 30 may transmit real time pressure measurements to the phone during the exhalation process, and the mobile application may display a gauge that displays these real time pressure measurements. The gauge may include an indication of the desired pressure range, and may display a needle or other visual indicator of the real time pressure so that the user can appropriately adjust his or her exhalation force to maintain the exhalation pressure within the desired range. The mobile application may also display a countdown timer that indicates the amount of time that the user should continue exhaling.

In embodiments in which the ketone measurement device 30 includes a temperature sensor 54, the process may also consider temperature as a secondary factor; for example, the process may ensure that the temperature remains within some threshold of normal body temperature (e.g., within 10%) for 8 seconds from commencement. If the exhalation does not satisfy the necessary condition or conditions (e.g., the user stops exhaling too soon or does not exhale with a sufficiently consistent force), the ketone capture device outputs an error indication (block 116) and terminates the process.

In embodiments that include a buzzer 201 (shown in FIG. 12) or other sound generator, the ketone capture device 30 outputs sounds that audibly convey status changes to the user during the above-described process. For example, a brief tone or other sound may be generated whenever the LED/status indicator 40 changes color. The tone, sound duration, and/or pattern of this sound may correspond uniquely to the particular status or event; for example one sound may be generated when the device 30 is ready for the user to begin exhaling, and another sound may be used to notify the user that they can stop exhaling. The sound generator 201 may also be used to notify the user in real time whether they are exhaling with sufficient pressure. Different sounds may also be generated for different respective error conditions. In some embodiments, the sounds may include pre-recorded or computer-generated voice messages.

Although not illustrated is FIG. 8, at the end of the exhalation process (whether successful or not), the process preferably switches the valve 44 back to the open position in which exhaled breath is vented from the device 30 via flow path 1 (FP1 in FIGS. 4 and 5). For example, if the user exhales for the target duration of 10 seconds, the ketone capture device preferably opens the valve 44 so that no additional breath is routed through the cartridge if the user continues to exhale. This feature, combined with the test for minimum exhalation conditions in block 110, ensures that approximately the same amount of breath passes through the cartridge 32 with each valid test.

During the exhalation process, the ketone capture device 30 may use the real time pressure measurements in combination with the exhalation time to determine whether and when the desired volume of breath has passed through the cartridge 32. For example, the processor may maintain a running total of the estimated volume of breath that has passed through the cartridge; once the desired volume is reached, the ketone capture device may open the valve (to prevent additional breath from passing through the cartridge) and/or signal the user to stop exhaling. With this feature, the target exhalation time may automatically be shortened when the user blows hard, and vice versa.

The inventors have discovered that the likelihood of the user completing an exhalation of sufficient duration can be increased significantly by notifying the user of how much longer they need to exhale. Thus, in some embodiments, during the exhalation process, the ketone capture device 30 and/or the mobile application outputs an indication how much longer the user needs to exhale. This indication may, for example, be a visual, audible, or haptic signal that is output by the ketone capture device 30 when a selected amount of time, such as one second or two seconds, remains before exhalation is complete. For instance, an LED that is visible during exhalation may be illuminated in a particular color or strobed at this point in time. As another example, the mobile application may display a numerical countdown timer, or may display a graphical indication of the amount of time remaining. In embodiments in which the user is required to exhale a threshold volume of breath, the ketone capture device's processor may determine or estimate the amount of time remaining based on the output of the pressure sensor 54 or a flow sensor. In embodiments in which the user is required to exhale for a fixed amount of time, the processor may determine the amount of time remaining based solely on a timer that is started when the user begins to exhale.

If the user is determined in block 114 to have completed a satisfactory exhalation, the ketone capture device outputs a "success" indicator (block 118), such as by switching the LED indicator 40 to a different color such as green. In non-standalone embodiments, the user would then use the eject button 38 to release and remove the cartridge 32; the user would then insert the cartridge into the separate base unit (FIG. 19) for analysis.

In standalone embodiments, the ketone capture device in block 118 instead initiates a cartridge analysis process in which it repeatedly measures the color or color change within the cartridge using the LED/photodiode assembly 48A, 48B during an analysis period. The analysis period is typically about 1 to 2 minutes, depending upon the interactant used. The ketone capture device then transmits the resulting measurement data (which may include a ketone measurement or data which can be used to generate the ketone measurement) to the phone. The LED indicator 40 may use a particular color, such as yellow, to indicate that the analysis process is taking place, and may change the color (and optionally enable the ejection button) when the analysis is complete. Depending upon the type or types of sensors 54 included, the ketone capture device may also transmit various other types of data to the phone with the ketone measurement data, including, for example, exhalation duration and measurements of pressure, temperature, carbon monoxide and carbon dioxide.

Once the process of FIG. 8 is complete, the ketone capture device 30 enters into a low power state in which it waits for a new cartridge 32 to be inserted.

The measurement data collected over time from exhalation events, including exhalation duration and exhalation success/fail events, may be used to adjust the breath ketone capture parameters used by the ketone capture device. For example, if the user fails to meet the minimum exhalation duration a threshold percentage of the time, the ketone capture device may lower the minimum exhalation duration for this user.

Although not illustrated in FIG. 8, the ketone capture device 32 may, during the illustrated process, notify the mobile phone of various state transitions, allowing the mobile application to display appropriate status and error messages. Examples of such messages include "begin exhalation," "continue exhaling for 10 seconds," "exhale with greater force," "exhale with more consistent force," "exhale for 2 more seconds," "you did not exhale long enough—please discard cartridge and repeat process with a new cartridge," "exhalation complete: remove cartridge and insert into base unit," "exhalation complete—analyzing cartridge," and "cartridge analysis complete—remove and discard cartridge." Example screen displays that may be presented are shown in FIG. 11, which is discussed below.

Several aspects of the above-described process for FIG. 8 contribute to the ease with which users can take ketone measurements. First, the user need not turn ON the ketone capture device 30 before inserting the cartridge 32; instead, the device 30 stays in a low power state when not in use, and initiates the process when a cartridge 32 is inserted. Second, the user need not launch the mobile application from the phone; instead, the mobile application is launched or brought to the forefront automatically in response to the user turning ON the ketone capture device 30. Third, the user need not perform any action to cause the valve to switch during the exhalation process; rather, the device 30 automatically switches the valve once the user has properly exhaled for a sufficient time period. Fourth, the ejection button facilitates removal of the cartridge, and (in some embodiments) provides a mechanism for inhibiting the user from prematurely removing the cartridge. Fifth, in standalone embodiments, the user need not move the cartridge to a separate unit for analysis. Sixth, the user preferably does not have to interact with the mobile application during the measurement process. Seventh, the system reduces poor quality ketone measurements by monitoring the exhalation process.

The processor-controlled task of analyzing the cartridge 32 after the exhalation event—whether performed by the ketone capture device or the base unit—preferably involves illuminating the cartridge with an array of LEDs of different light frequencies while generating measurements, with a photodiode, of light reflected from the interactant chamber of the cartridge. The resulting light measurements generated by the photodiode are then converted into a measurement value representing the concentration of the ketone of interest in the breath sample. The program code that generates this measurement may, in some embodiments, compensate for the actual exhalation duration and/or the measured pressure (e.g., average exhalation pressure following valve closure). For example, if the target exhalation duration is 10 seconds but the user only exhales for 8.2 seconds, the program code may bump or scale the ketone measurement upward to compensate for the reduced quantity of breath passing through the cartridge 32. As another example, if the target exhalation pressure is 18 psi, and the user exhales for 10 seconds with an average pressure of 17 psi, the process may similarly bump or scale upward the measurement to compensate for the reduced flow of breath passing through the cartridge 32 during the exhalation.

The program code that performs this conversion of optical measurements to a ketone concentration measurement may, in some embodiments, be executed by a device that is separate from the device that generates the optical measurements. For example, the ketone capture device or base unit may send the optical measurements to the user's phone, which may then convert these measurements to a ketone measurement value or may transmit them to a remote server that generates the ketone measurement value.

The exploded views in FIGS. 7A and 7B show a printed circuit board 60 of the ketone capture device. The printed circuit board preferably includes a microcontroller or other processor, a memory (which may be built into the processor), a Bluetooth or other wireless transceiver, a rechargeable battery, and circuitry for integrating with the various sensors of the device. The printed circuit board 60 is preferably capable of monitoring the ejection button 38 so that the ketone capture device and phone can determine when the cartridge has been ejected. In standalone embodiments, the printed circuit board 60 may also include the photodiode/LED assembly (see FIGS. 13 and 14, discussed below).

Figure 9:
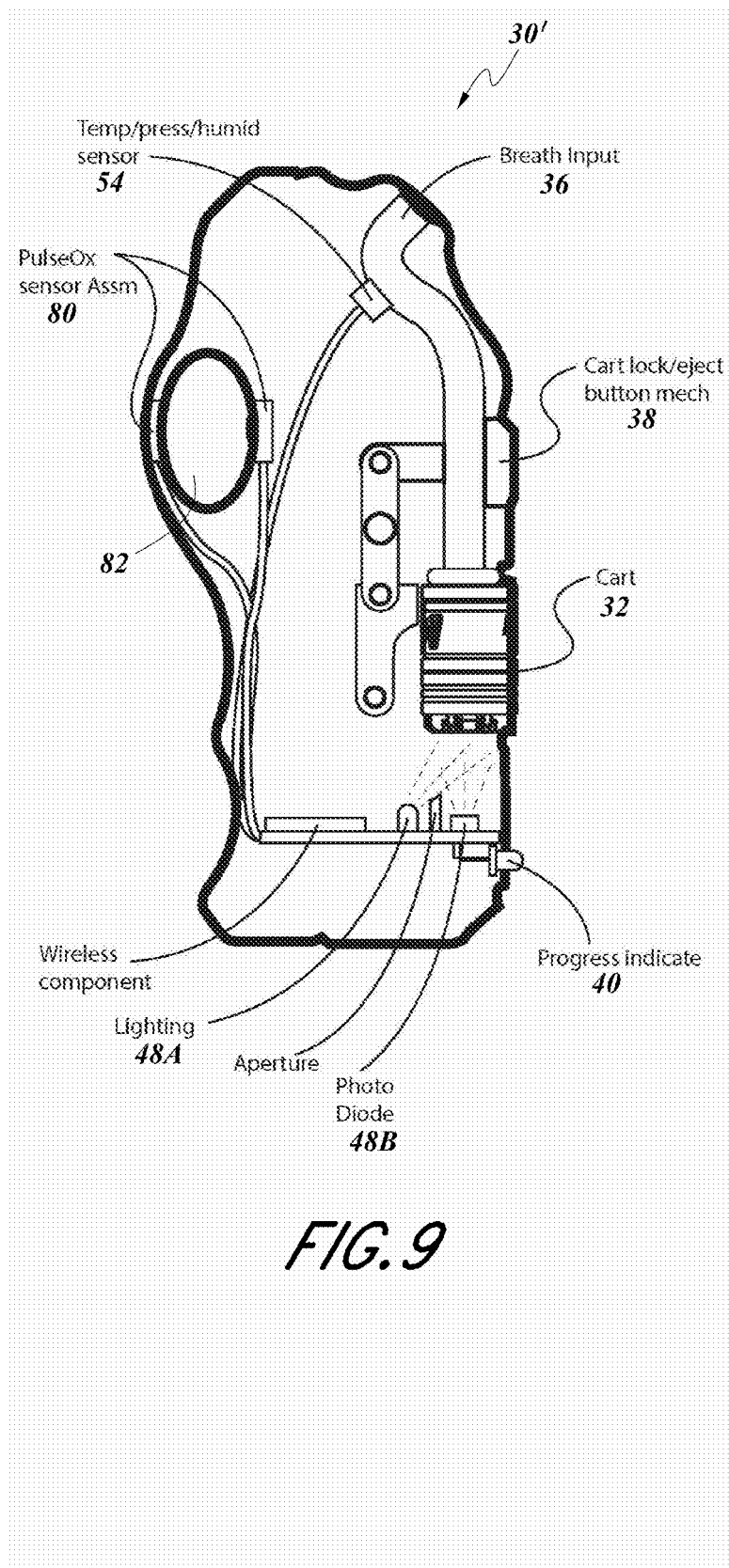
FIGS. 9 and 10 illustrate a multi-function "bedside unit" embodiment that includes a pulse oximeter.
Figure 10:
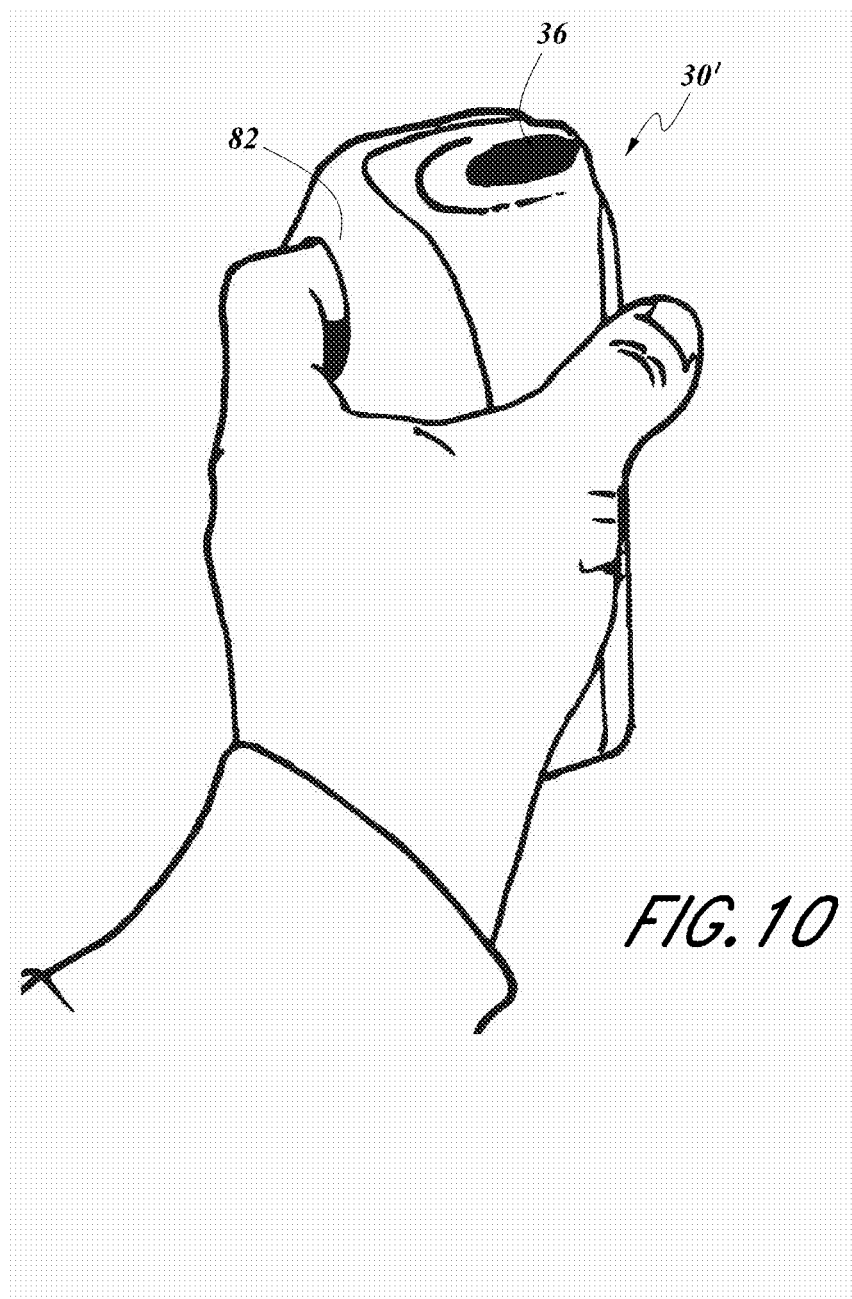

FIGS. 9 and 10 show a multi-function embodiment 30' that, in addition to the components described in the preceding embodiments, includes a pulse oximetry assembly 80. In this embodiment, the ketone capture device 30' is a standalone device, meaning that it includes the necessary hardware and firmware components (preferably including an LED array 48A and photodiode 48B) for analyzing the cartridge 32 after exhalation. These cartridge-analysis components may alternatively be omitted, in which case the multi-function device 30' may be used in combination with a base unit. As is conventional, the pulse oximetry assembly 80 includes an infrared light source that passes infrared light through a finger of the user, and includes an infrared sensor that measures infrared light emanating from the opposite side of the finger.

The ketone capture device shown in FIGS. 9 and 10 is preferably a bedside unit that can be used when a user wakes up in the morning. Specifically, after waking up, the user may grasp the unit with one hand, as shown in FIG. 10, such that the index finger passes through the opening 82. (The unit 30' may be configured to initiate the testing process either in response to cartridge insertion or in response to detecting finger insertion, depending on the embodiment.) In some embodiments, the ketone capture device 30' initially measures the user's resting pulse, and upon generating a resting pulse measurement, indicates via the status indicator 40 that the device 30' is "ready" to receive the user's breath sample. The user can then exhale the breath sample into the breath input port 36. In other embodiments, the ketone capture device 30' measures the user's pulse during the exhalation process. The operation of the ketone capture device 30' may otherwise be the same as described above, except that the unit 30' additionally transmits pulse oximetry data to the mobile phone and app.

FIG. 11 illustrates example screens and messaging that may be presented during and following the breath capture process of FIG. 8. In this example of FIG. 8, it is assumed that the ketone capture device measures the acetone content, temperature, and carbon monoxide content of the breath sample, and also measures the user's heart rate and SPO2 (peripheral capillary oxygen saturation) via a pulse oximeter device. When the user initially inserts the cartridge 32 into the ketone capture device, the mobile phone brings to the forefront the mobile application, which displays a screen indicating that cartridge insertion is detected and which instructs the user to start exhaling. As shown in the next three screens of the sequence (which are displayed during exhalation), the mobile application displays status information (as reported in real time by the ketone capture device) regarding the physiologic parameters being detected. ("Smoking" in this example corresponds to carbon monoxide detection.) The fifth screen in the sequence indicates that the exhalation process was successful and indicates the duration of the exhalation. The sixth screen shows the user's acetone measurement (8 parts per million) and weight (as entered by the user or captured via a wireless scale), and shows graphs of the user's weight and acetone levels over the last eight measurement cycles (with weight trending downward and acetone level trending upward). The last screen in the sequence displays all of the key measurements taken during the exhalation process. As mentioned above, various other physiologic measurements may additionally or alternatively be collected, such as measurements of $CO_2$, ethanol, ammonia, isoprene, etc.

As discussed above, the mobile application may also display real time pressure data during the exhalation process, together with a target pressure or pressure range. This feature enables the user to maintain the desired pressure throughout the exhalation process, such that the volume of breath passed through the cartridge 32 during exhalation events is approximately equal from test to test.

The mobile application may also include user interfaces and executable code for implementing various other features, such as the features described in U.S. Pat. Nos. 9,351,684 and 10,068,494, the disclosures of which are hereby incorporated by reference. For example, the mobile application may provide the user with diet recommendations and other health coaching tips that are dependent upon the acetone measurements and/or other measurements generated by the ketone capture device, as described in the '494 patent referenced above.

Electronic Components of Ketone Capture Device

Figure 12:
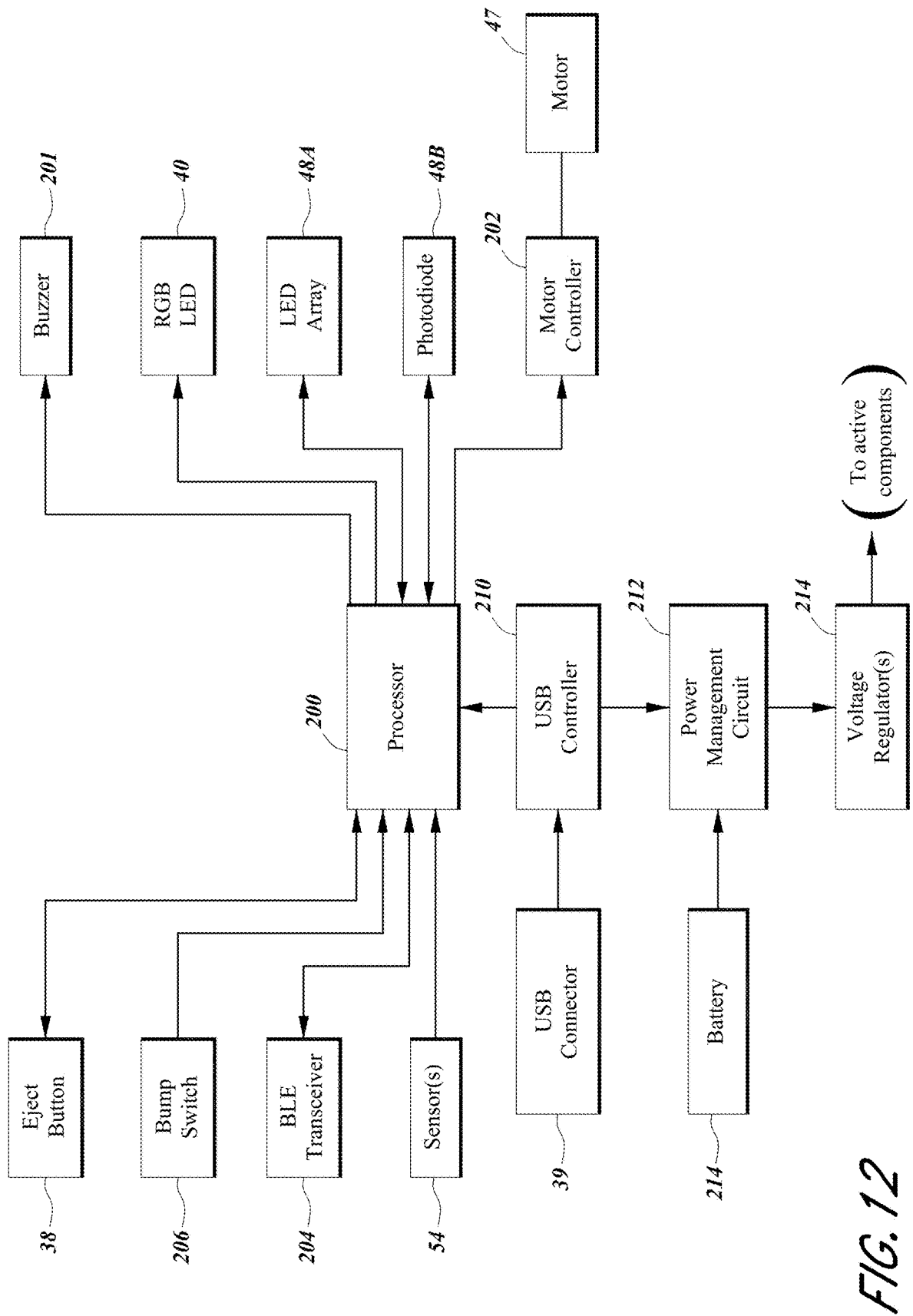
FIG. 12 is a block diagram of the circuitry that may be included in the ketone capture devices of the preceding figures.

FIG. 12 illustrates the primary electronic components that may be included in the ketone capture devices 30, 30' described above. The illustrated components include a programmed processor 200 that controls the following components: a buzzer 201 (used to output audible status indicators), a RGB LED 40 (used to display status information as described above), the LED array 48A (included in standalone embodiments), a motor controller 202 (that controls the motor 47 used to control the state of the valve 44), and a BLE transceiver module 204. The processor also receives signals from the ejection button 38, a bump switch 206 (used to detect cartridge insertion), the one or more sensors 54, a USB controller 210, and the photodiode 48B (included in standalone embodiments). The bump switch 206 may be replaced with another type of presence sensor, such as a photodiode, that is capable of detecting the presence of a cartridge 32. The circuitry also includes a power management circuit 212 that receives a power signal from a rechargeable battery 214. The power management circuit 212 provides an output voltage to one or more voltage regulators 214, which supply regulated voltage signals to the various active components.

One example of a processor 200 that may be used is the PIC18F46K22 Microcontroller from Microchip Technology. The responsibilities of the processor 200 include sending data to the BLE transceiver module 204 to transmit, determining that a cartridge is inserted, monitoring the sensors (e.g., to determine whether the exhalation characteristics meet the requirements for a valid exhalation), activating the motor 47 (to control the valve 44), and outputting status information to the user. As mentioned above, the processor may also be programmed to control the volume of breath that passes through the cartridge 32 (or that passes by a nanoparticle or other semiconductor sensor), such as by monitoring the exhalation pressure and controlling the state of the valve 44. In standalone embodiments, the processor also controls the LED array 48A, and may use the associated data collected from the photodiode 48B to generate a ketone measurement value. One example of a BLE transceiver module 204 that may be used is the BLE112 Bluetooth Smart Module from Silicon Labs.

When the ketone capture device 30 is in a low-power state, the BLE transceiver module 204 preferably remains ON while the processor 200, voltage regulators 214, and other active components are maintained in an OFF or low-power state. When the BLE module 204 establishes a connection, its firmware preferably causes it to generate a signal that causes other active components to be powered up. This may be accomplished in a variety of ways. For example, the BLE module 204 may send a signal to the processor 200 using an appropriate protocol (such as UART, SPI, I2C, GPIO), and the processor may respond by transitioning out of its low-power state and by powering up the other active components of the system. As another example, the BLE module could send a GPIO signal that turns on a global power regulator or transistor, causing power to be provided to the processor 200 and other active components. The processor 200 may be configured to switch the device 30 back to a low-power state after a threshold period of inactivity.

In some embodiments, the processor 200 may also (or alternatively) transition out of a low-power state upon receiving a signal from the bump switch 206, so that the device 30 effectively wakes up in response to cartridge insertion.

The firmware (program code) executed by the processor 200 and BLE module 204 may be stored in non-volatile memories included in these devices or in any other type of non-transitory computer readable media.

Photodiode/LED Assembly

Figure 13:
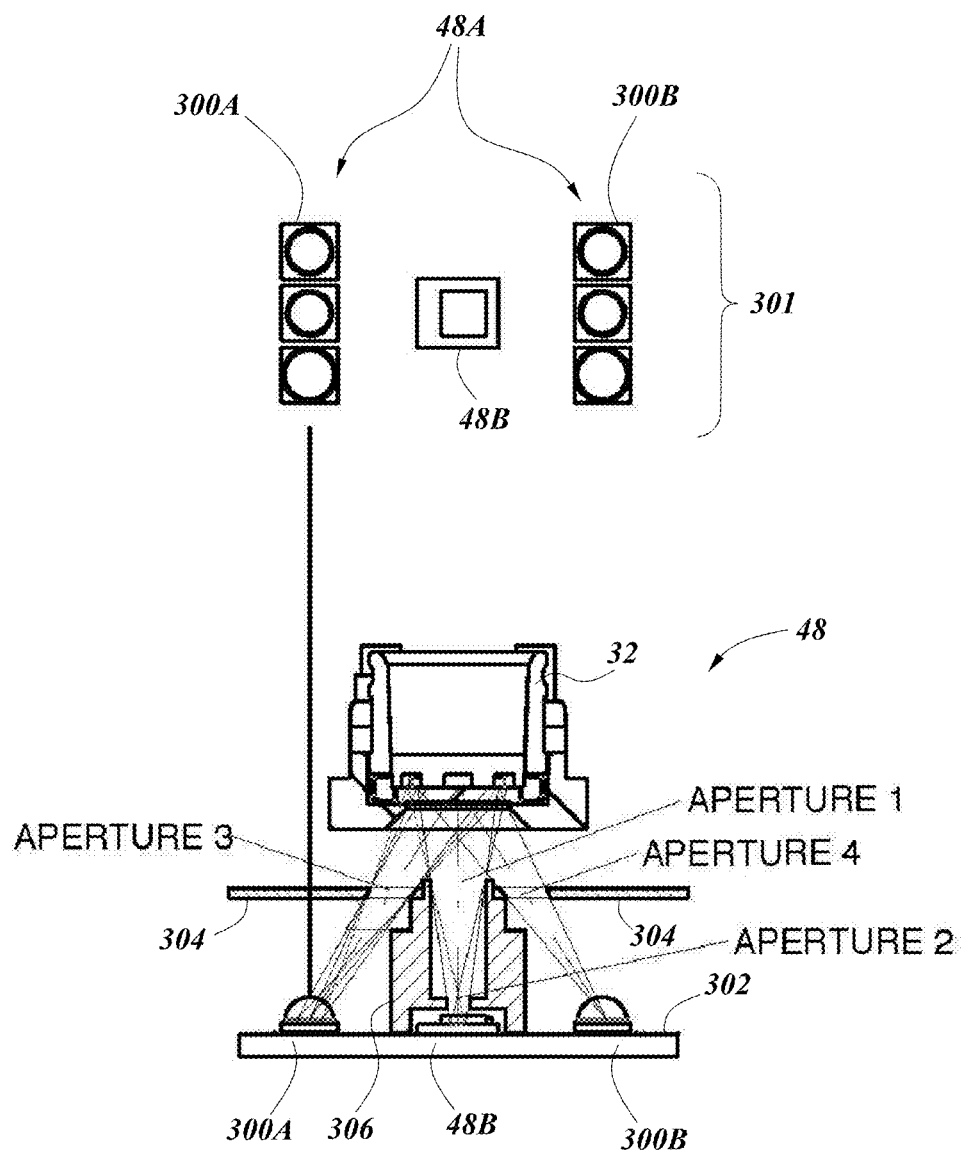
FIG. 13 shows a top view and a side view of an LED/photodiode arrangement according to one embodiment.

FIG. 13 shows one embodiment of the LED/photodiode assembly 48, including structures that substantially limit the light that reaches the photodiode 48B to light reflected directly from the cartridge 32 (through a lens of a lens cap) after coming directly from the one or more LEDs. The illustrated assembly may be included either in a standalone ketone capture device 30, 30' or in a separate base unit. In the illustrated embodiment, the LED array includes two rows 300A, 300B of LEDs, each of which contains three LEDs. In other embodiments the LED array 48A may consist of a single LED, of two LEDs, or of any other number of LEDs. The LEDs 48A and photodiode 48B are mounted to a printed circuit board 302.

The upper portion 301 of FIG. 13 shows a top-down view of the assembly, and the lower portion shows a side view. In this embodiment, the LEDs of each three-LED row are arranged linearly. In an embodiment shown in FIG. 14 and described below, the LEDs of each row are arranged in a semi-circle. The lightly drawn lines in the lower portion of FIG. 13 illustrate beams of light to and from the cartridge 32.

Referring to FIG. 13, the assembly includes an opaque light shield 304 that blocks unwanted light from the LEDs from reaching the cartridge 32 via indirect paths, so that substantially all of the light that enters and illuminates the cartridge 32 through its transparent window or lens comes directly from the LEDs. The light shield 304, which may be formed from plastic, metal, or a variety of other materials, includes three apertures, labeled as apertures 1, 3 and 4. Aperture 3 is configured to enable light from LED row 300A to directly illuminate the cartridge 32, and aperture 4 is configured to enable light from LED row 300B to directly illuminate the cartridge. Aperture 1, when viewed from the top (not shown but generally similar to FIG. 14), may appear as three circular or oval holes that overlap with each other (with each hole corresponding to a respective LED), and aperture 3 may have the same configuration.

Aperture 1 in FIG. 13 is configured to block light that reflects off of surfaces other than the cartridge 32 from reaching the photodiode 48B. The assembly also includes a bowl-shaped member 306 that includes an additional aperture, labeled aperture 2, that blocks light reflected from the cartridge 32 from reaching the photodiode 48B via an indirect path.

The light-blocking structures 304, 306 shown in FIG. 13 improve the accuracy of measurements by reducing the impact of stray light that reflects off internal surfaces of the ketone capture device 30. Various other types of structures, such as light tubes and/or mirrors, may be additionally or alternatively be used for this purpose.

Figure 14:
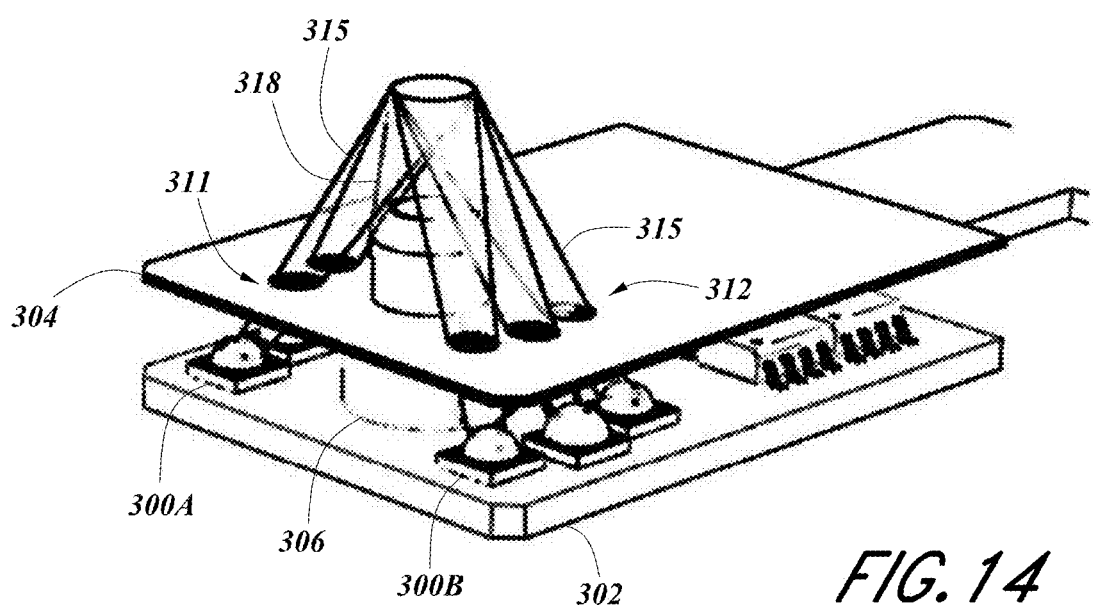
FIG. 14 is a perspective view of another embodiment of the LED/photodiode arrangement.

The embodiment of FIG. 14 is similar to that of FIG. 13, except that (1) the LEDs of each three-LED row are arranged on the printed circuit board 302 in a semicircular arrangement instead of a linear arrangement, and (2) as a result of this arrangement, aperture 3 in FIG. 13 is replaced with three distinct apertures 311 (each corresponding to a respective LED and having an oval or circular configuration), and aperture 4 in FIG. 13 is similarly replaced with three distinct apertures 311. Conical beams of light 315 are shown in FIG. 14 from the respective LEDs to the cartridge 32 (although the cartridge itself is not shown), and a generally cylindrical beam of light 318 is shown reflecting off the cartridge 32 (through its window or lens) in the direction of the photodiode. The view of the photodiode is obstructed in FIG. 14 by the bowl 306.

The number and arrangement apertures (or other beam-forming structures) will generally depend on the number of LEDs used. For example, in another embodiment (not shown), each row 300A, 300B is replaced with a single respective LED to form a two-LED array (each of which may operate at a different wavelength), and the light shield 304 includes a respective circular or oval shaped aperture for each LED.

In some embodiments, at least some of the LEDs of the LED array 48A operate at (emit light with) different wavelengths than other LEDs in the array. The array of LEDs may operate in the range of 300 to 800 nanometers (nm), and more preferably in the range of 350 to 740 nanometers. For example, in an embodiment for measuring acetone, the LED array is composed of the following six LEDs: two LEDs that operate at 475 nm, two that operate at 588 nm, and two that operate at 730 nm. In this embodiment, the photodiode 48B is preferably a blue color-enhanced 660 nm device that operates in the range of 400 to 1100 nm. The primary range of measurement is preferably 470 to 740 nm.

In embodiments capable of measuring multiple analytes, a broader spectrum of LEDs is preferably used; for example, the array may be composed of 350 nm, 458 nm, 525 nm, 615 nm and 730 nm LEDs. The photodiode 48B in such embodiments may, for example, operate in one of the following ranges: 350 to 750 nm, 450 to 700 nm, 450 to 575 nm, or 350 to 650 nm.

In one embodiment, the processor 200 is programmed as follows to use the LED array 48A and photodiode 48B to monitor the chemical reaction within the cartridge 32. (This same process can be implemented in a separate base unit in non-standalone embodiments.) Every three seconds during an analysis period, a measurement cycle is performed in which the LEDs are sequentially turned on (for no more than a few milliseconds) and then off such that only the LEDs of a particular wavelength are on at any given time. For example, in one embodiment that includes 730 nm, 588 nm and 475 nm LEDs, the 730 nm LEDs are switched on and then off; the 588 nm LEDs are then switched on and then off; the 475 nm LEDs are switched on and then off, and then all LEDs are kept off for the remainder of the 3 second cycle. The cycle is then repeated, and the process continues until the analysis cycle ends. Each time the LED(s) of a particular wavelength are turned on, the photodiode is used to take an intensity measurement. At the end of the analysis period, the processor 200 has reflectance trends for each LED wavelength. The processor 200 (or a separate processor, such as the processor of the mobile phone) divides the analysis period into kinetic stages and computes ratios between the measurements at different wavelengths. The differences between the averages of the ratios are computed with a standard calibration curve to generate a final ketone measurement. The length of the analysis period, and the specific computations performed, typically depend upon the chemical composition of the interactant within the cartridge and on whether a developer solution is used.

In one embodiment in which three LED wavelengths (colors) are used (e.g., two LEDs of each wavelength), the ketone level is determined from the photodiode measurements as follows:

(1) Take the average of (LED3/LED2−LED2/LED1) over a selected time period, such as t=10 seconds to t=40 seconds, wherein LEDx is the intensity reading when the LEDs of wavelength x are illuminated. For example, if blue, red and yellow LEDs are used, this "difference of ratios" equation may be (LEDblue/LEDred−LEDred/LEDyellow). The time period may be selected based on the particular chemical reaction that occurs; for example, it may be selected to capture the point in time at which a color change progresses from yellow to blue. Different time ranges may be used for different analytes.

(2) Compare the average calculated in (1) to a calibration curve or look-up table generated using test samples containing known quantities of acetone (or whatever analyte is being measured).

In some embodiments, the different cartridges 32 (or different sections of the same cartridge) are used to measure different analytes using different respective interactants. In these embodiments, the particular LED wavelengths used may depend on the analyte being measured and the respective interactant used. Thus, the LEDs and LED wavelengths used in the assembly 48 may be selected to work with multiple interactants and associated chemical reactions.

Mobile Application Behavior

The following is a description of a preferred embodiment of the mobile application and of its use of BLE to communicate with the ketone capture device 30.

The mobile application is configured to run in the background and to receive BLE event notifications from the mobile device operating system of the phone. This is accomplished through the mobile application's configuration file that is compiled with the executable and read by the mobile device's operating system when the mobile application is launched. When the mobile application is launched by the user, it registers a series of callback functions to be invoked upon certain BLE events, for example, when a new message is received or when a new device is found. The mobile application also instructs the operating system to continue to scan for devices while the mobile application is running in the background.

When a cartridge 32 is inserted into the ketone capture device 30, the ketone capture device 30 wakes up and begins broadcasting, via the BLE transceiver, its presence to be discovered by the mobile application running on the phone. While the mobile application may be notified that the ketone capture device 30 has connected, many mobile operating systems prevent apps from bringing themselves to the foreground as this may lead to confusing behavior for the user. For mobile operating systems that include this limitation, the mobile application instead sends itself a notification that appears on the phone just like an email or text message notification. This message will also appear on the lock screen. When the user taps on the message, the mobile application is brought to the foreground. When the mobile application is brought to the foreground, the operating system passes to it certain information which can be used by the mobile application to render the appropriate screen (see FIG. 11). For example, it will automatically display the screen involved in the user using the ketone capture device 30.

To conserve power, many operating systems reduce the speed at which BLE events are processed and delivered to applications. To prevent the mobile application from "missing" certain BLE events, the ketone capture device 30 may, in some embodiments, buffer status data and periodically attempt to re-send it. Additionally, the ketone capture device 30 may never shut off its BLE transceiver to maximize the chance that the phone and the ketone capture device 30 will connect with one another while the user is preparing to use the ketone capture device.

In system embodiments that include a base unit (FIG. 19), the mobile application, upon being launched, starts searching for a base unit to connect with, and continues the search until a base unit is found. When the base unit disconnects, the mobile application starts searching again for a base unit. The mobile application searches for a ketone capture device 30 to connect with in the same manner.

Other Ketone Sensor Types

In the embodiments described above, the ketone level is determined by measuring the reflectance/absorption characteristics of the interactant material in the disposable cartridge 32. In other embodiments, other types of ketone sensors may be used. For example, other types of chemistry-containing disposables may be used, such as an enzyme test strip that is inserted into an electrochemical receiving area of the device 30. Further, the disposable cartridge 32 and LED/photodiode assembly 48 can be replaced with a semiconductor sensor, such as a nanoparticle sensor, that senses acetone and/or other ketones. Examples of other types of sensors that may be used are disclosed in U.S. application Ser. No. 15/156,188, filed May 16, 2006, the disclosure of which is hereby incorporated by reference.

In embodiments that include a nanoparticle sensor or other semiconductor sensor, it is desirable to control the flow rate of breath that is exposed to the sensor during exhalation. Thus, the various features described above involving the monitored exhalation pressure and time still apply. For example, the device 30 may monitor both the exhalation time and pressure (and optionally temperature) to determine whether the exhalation is sufficient, as described above. As another example, the mobile application may display real time pressure data to the user during the exhalation process to assist the user in maintaining the desired pressure. The various features described above involving the opening and closing of the valve 44 are also applicable in nanoparticle/semiconductor sensor embodiments, but for the purpose of controlling which portion of the user's exhaled breath sample is exposed to the sensor.

Cartridge Design

A preferred embodiment of the cartridge 32 will now be described with reference to FIGS. 15-18. Additional details of the illustrated embodiment are included in U.S. Provisional Appl. No. 62/675,109, filed May 22, 2018, the disclosure of which is hereby incorporated by reference.

Figure 15A:
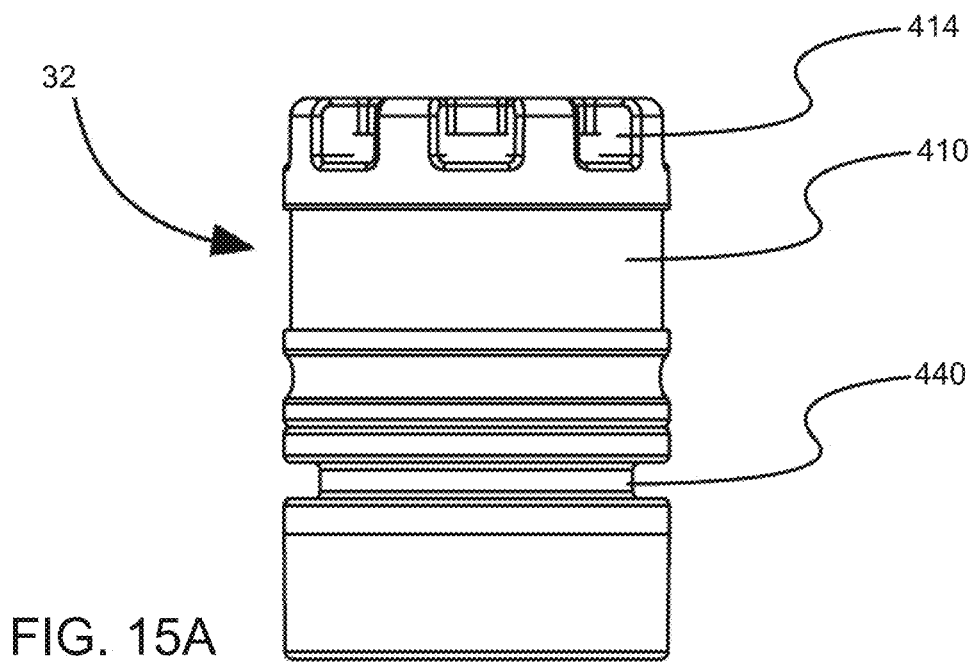
FIGS. 15A-15D show various views of an embodiment of a breath sample capture cartridge. Specifically.
Figure 15B:
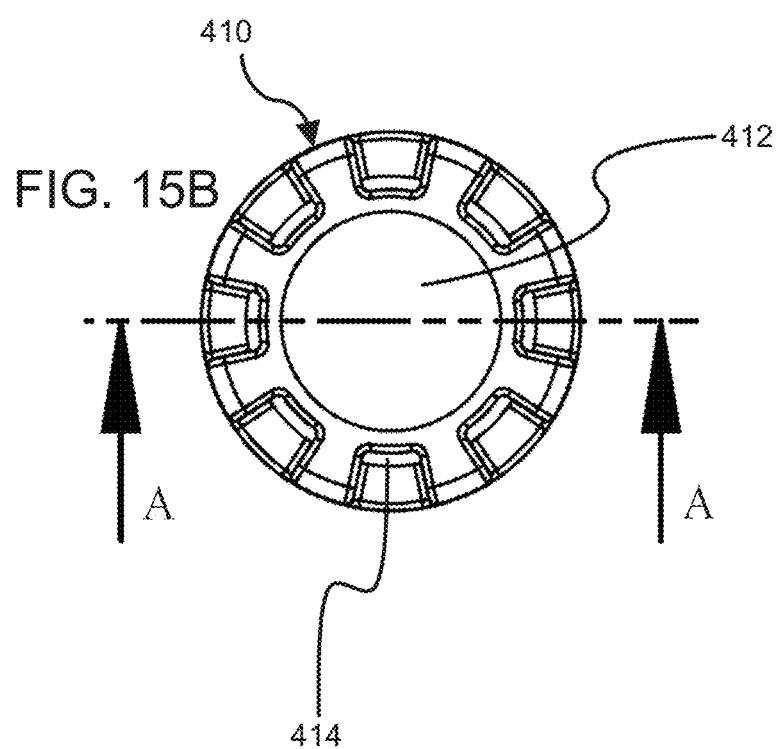
Figure 15C:
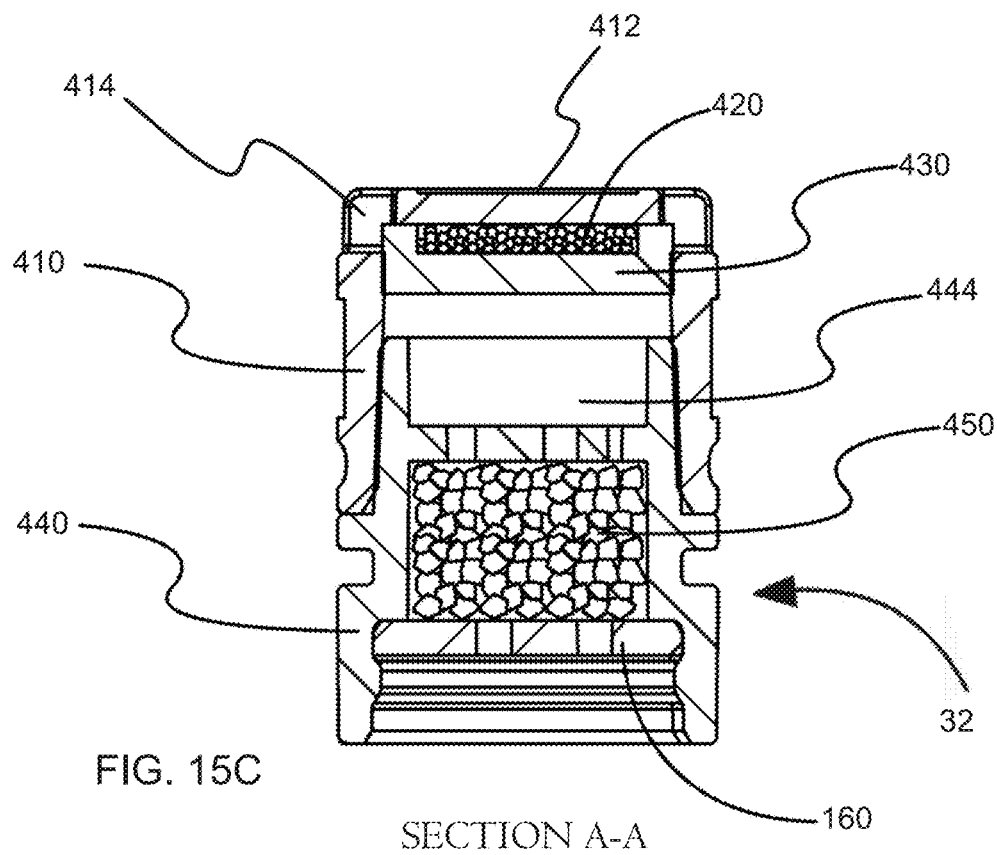

The cartridge 32, as shown in FIG. 15A, includes a cartridge lens cap 410 that has a number of lens cap vents 414 and fits on a cartridge desiccant canister 440, e.g., fits securely on the cartridge desiccant canister 440. FIG. 15B is top view of the cartridge 32, showing the cartridge lens cap 410 surrounded by several, e.g., eight, lens cap vents 414. FIG. 15C illustrates a sectional view of the cartridge 32 taken along line A-A. A quantity of interactant 420 resides in the interior of the porous bowl 430. The porous bowl 430 containing the interactant material 420 is fit into the cartridge lens cap 410 such that the edges of the porous bowl 430 prevent the interactant 420 from falling out of the lens cap vents 414 of the cartridge lens cap 410. The lens cap 410 includes a transparent window or lens 412 that is configured to (1) direct incoming light from the LEDs into the reactive chamber containing the interactant, and (2) direct light reflected back from the interactant to the photodiode.

The cartridge lens cap 410 (already containing the porous bowl 430 containing the interactant 120) is fitted onto the cartridge desiccant canister 440. The cartridge desiccant canister 440 contains a quantity of desiccant 450 held in place, under a ported upper surface, by a cartridge desiccant retainer 460, which also has at least one port. Therefore, the cartridge 32 defines a continuous flow path therethrough. As will be understood with reference to FIGS. 15C and 17, in at least one embodiment, the continuous flow path proceeds from the base of the cartridge 32, into the bottom opening of the cartridge desiccant canister 440, through the ports of the cartridge desiccant retainer 460, through the desiccant 450 (held between the cartridge desiccant retainer 460 and the cartridge desiccant canister 440) through the ports in the cartridge desiccant canister 440, through the canister cavity 444, through the base of the porous bowl 430, through the interactant 420, through the sides of the porous bowl 430, and out through the lens cap vents 414. Various modifications to this flow path may be made.

Figure 15D:
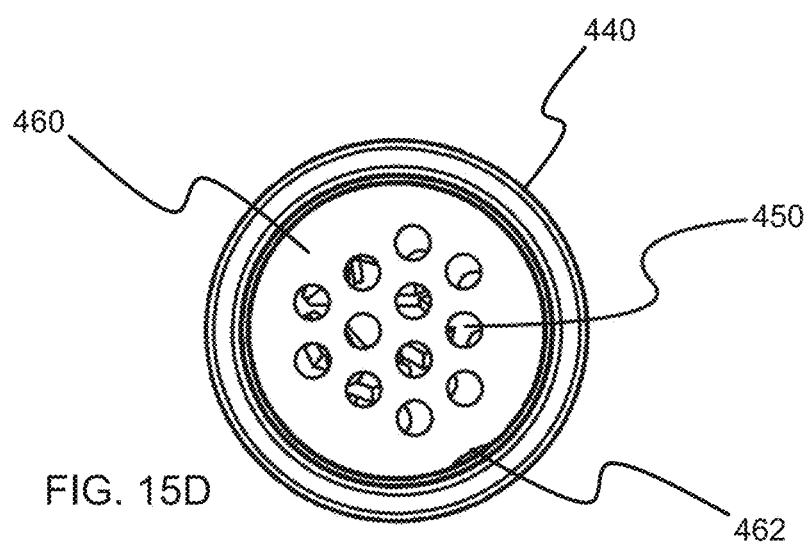

FIG. 15D illustrates the cartridge 32 from the bottom. The cartridge desiccant canister 440 may be seen, as well as the cartridge desiccant retainer 460 holding in a quantity of desiccant 450. Additionally, a desiccant retainer notch 462 may be seen.

The cartridge lens cap 410 is shaped generally like a cylinder and includes a lens cap window 412 and at least one lens cap vent 414. In some embodiments, the cartridge lens cap 410 may have shapes other than a cylinder. For example, the cartridge lens cap 410 may be have four sides, five sides, six sides, seven sides, eight sides, or any other number of sides. Circular cartridge lens caps 410 may advantageously simplify the manufacturing process, but one of ordinary skill in the art will easily understand that a cartridge lens cap 410 having other numbers of sides may be used. The cartridge lens cap 410 may have a diameter of between about 8.5-16 mm, between about 9-14 mm, between about 9.5-12 mm, or any other diameter that advantageously facilitates use and collection of samples as disclosed herein.

Figure 16A:
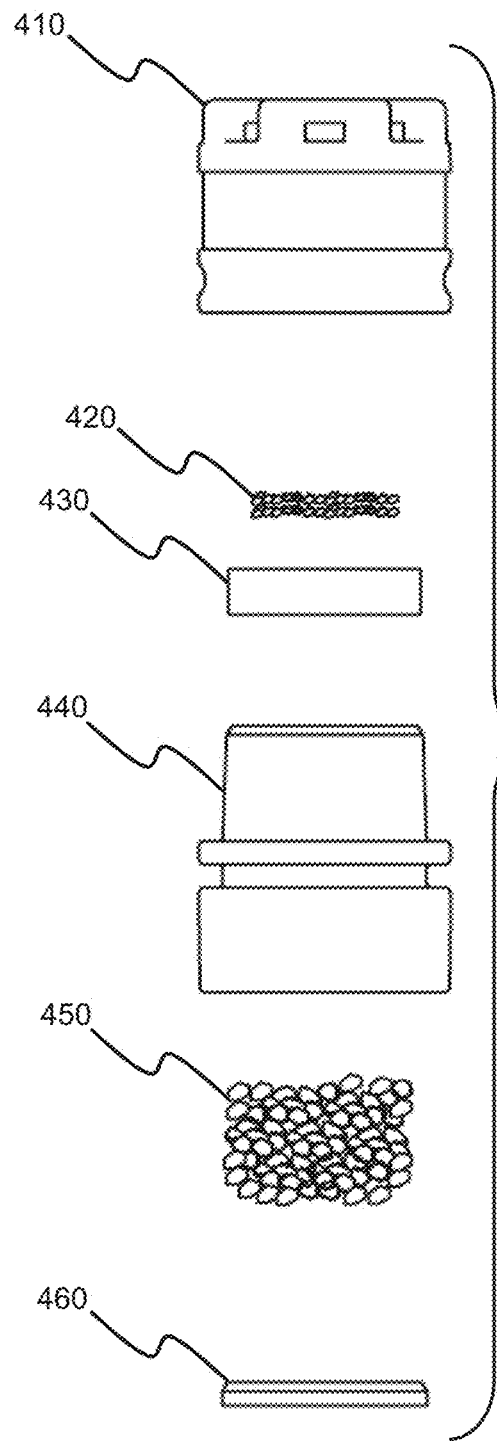
FIGS. 16A and 16B show exploded views of the cartridge of FIGS. 15A-15D.
Figure 16B:
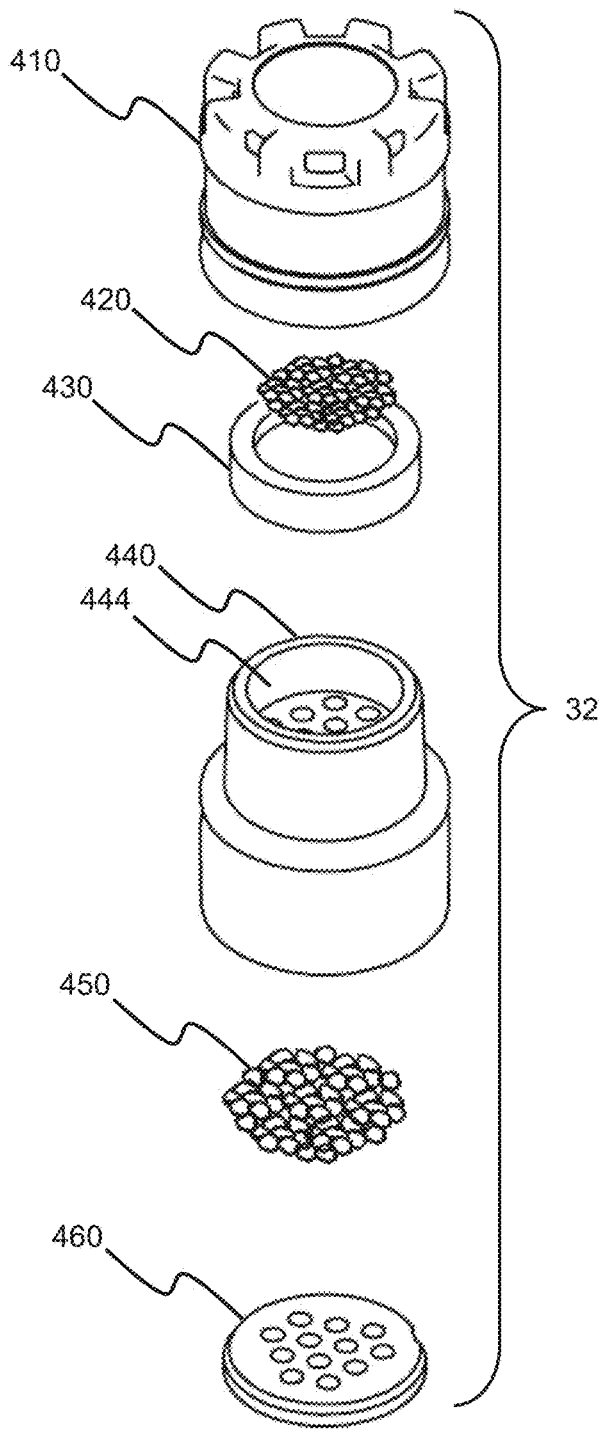
Figure 17:
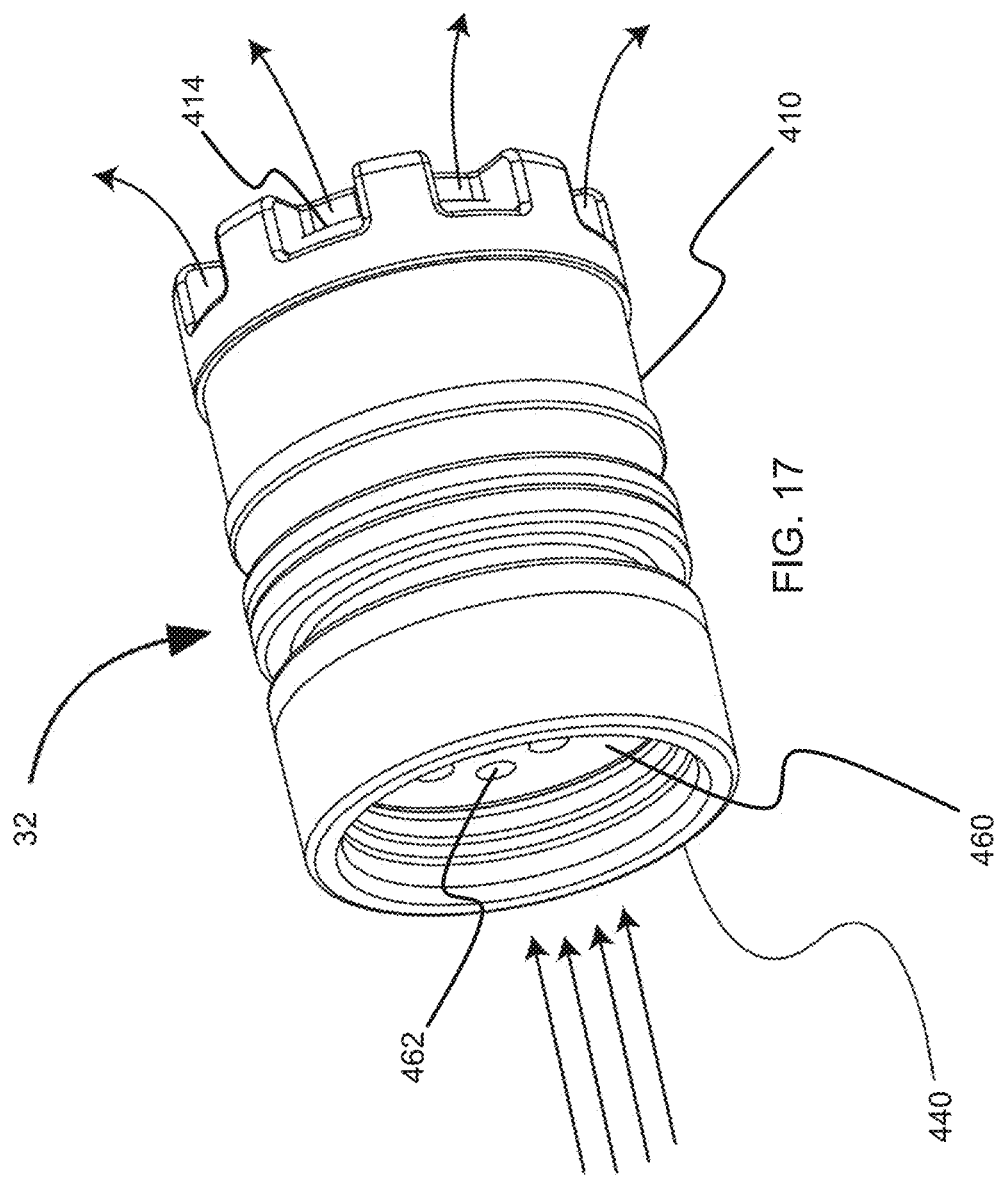
FIG. 17 shows a bottom-biased three-quarter view of the cartridge of FIGS. 15A-15D and shows an air path through the cartridge.

FIGS. 16A and 16B illustrate exploded views of the cartridge 32. The illustrated components include the cartridge lens cap 410, interactant 420, the porous bowl 430, the cartridge desiccant canister 440, desiccant 450 and the cartridge desiccant retainer 460. FIG. 15C illustrates how these components may fit together. The interactant may be in the form of functionalized beads, or may be in the form of a molded, porous bowl.

Figure 18A:
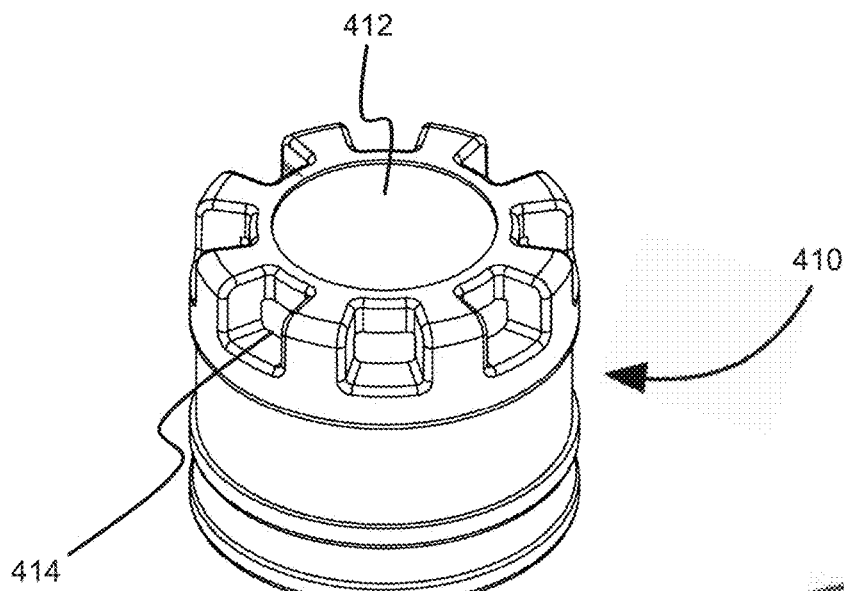
FIGS. 18A-18C show various view of a cartridge lens cap of the embodiment of FIGS. 15A-15D.
Figure 18B:
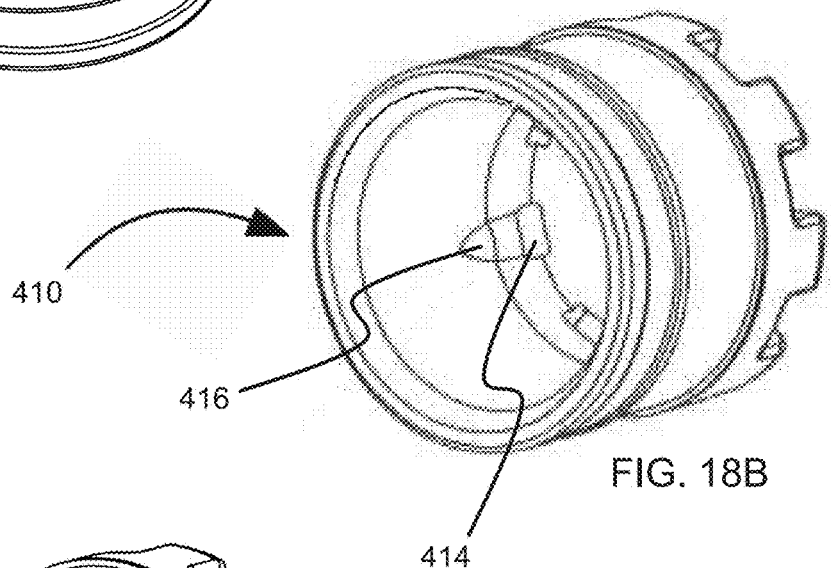
Figure 18C:
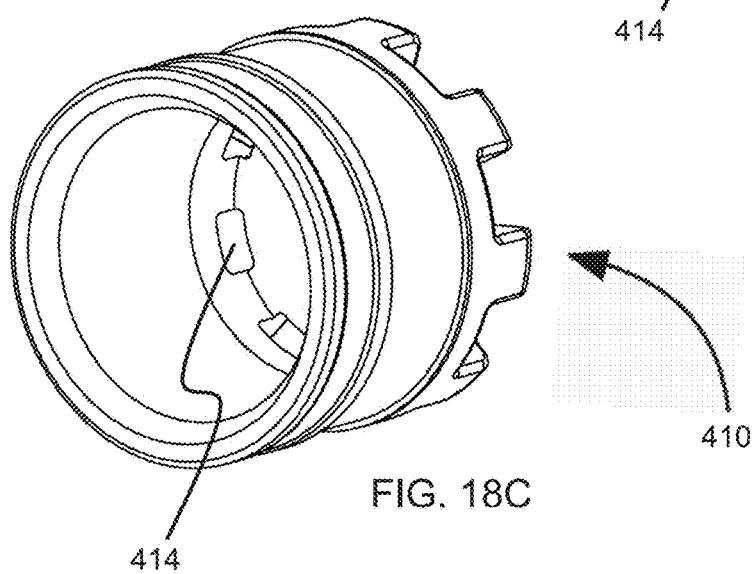

FIGS. 18A-C illustrate various views of the cartridge lens cap 410. As shown in FIG. 18A, the lens cap includes a lens cap window 412 surrounded by eight lens cap vents 114. FIG. 18B shows the lens cap 410 from the bottom such that at least three of the lens cap vents 414 and an undercut 416 may be seen. FIG. 18C shows a variation in which no undercuts 416 are included. The undercut(s) 416, if included, may be a partial conical surface with a flat upper surface facing the top of the cartridge lens cap 410. Undercuts 416 may augment or replace a continuous or partial smaller retention or holding feature. In some embodiments, the cartridge lens cap 410 has no retention or holding feature and retains the porous bowl 430 through friction. In other embodiments, the porous bowl 430 is held within the cartridge lens cap 410 by the top surface of the cartridge desiccant canister 440 pushing up against the bottom of the porous bowl 430 which holds the top surface of the porous bowl 430 against the inner surface of the top of the cartridge lens cap 410.

Base Unit

As mentioned above, in non-standalone embodiments, the ketone capture device 30 may be used in combination with a base unit. One embodiment of a base unit is shown in FIG. 19. In this embodiment, the base unit 500 includes a cartridge tray 502 that retracts into a housing of the base unit. The base unit 50 also preferably includes the following components that are not shown: (1) a developer solution dispensing assembly that dispenses developer solution from a container into the cartridge 32, (2) a Bluetooth (preferably BLE) transceiver, and (3) an LED/photodiode assembly of the type described above.

In operation, a user inserts a used cartridge 32 into the tray 502 and then pushes the tray into the housing. The base unit 500 then dispenses the developer solution into the cartridge, waits a sufficient time for a chemical reaction to occur, and then uses the LED/photodiode assembly to measure the color and/or intensity change produced by the reaction as described above. The base unit 500 then converts the optical measurements into a ketone measurement value and transmits this value via Bluetooth to the user's phone. The base unit 500 may alternatively transmit the optical measurements to the phone, in which case the phone or another computing device may perform the conversion.

Additional details of the base unit 500 are disclosed in U.S. application Ser. No. 15/156,188, referenced above.

Example Uses of Collected Data

In embodiments that collect multiple physiologic parameters, the collected parameters may be used in combination for various heath monitoring and coaching applications. For example, a ketone capture device that measures acetone and $CO_2$ can be used to implement a heath program that monitors fat metabolism (based on acetone) and energy metabolism (based on $CO_2$). These monitored parameters may be used to provide automated or semi-automated health coaching to the user. As another example, the ketone capture device may monitor beta-hydroxybutrate (BHBA) through the skin, and the BHBA levels may be used in combination with breath acetone levels. Examples of how blood-based and breath-based ketone measurements may be collected and analyzed in combination are disclosed in U.S. application Ser. No. 15/665,352, filed Jul. 31, 2017, the disclosure of which is hereby incorporated by reference.

The following are hypothetical examples of how the physiologic parameters measured by the ketone capture device may be used.

EXAMPLE 1

Jane has been on a low carbohydrate diet plan for 30 days and is ready to remove alcohol as a weight loss accelerant. Jane updates her weight loss plan in her mobile application to reflect the alcohol removal setting. Every breath test afterwards as Jane uses her ketone capture device to monitor her breath acetone levels to capture her fat metabolism, her ketone capture device will automatically capture and log her breath alcohol levels. The third day after Jane starts her alcohol removal accelerant plan, Jane has a work dinner and has 4 cocktails in the evening. The next morning, Jane's breath alcohol levels reflect a >0.05 BAC and the previous day is noted as a non-compliant day and Jane does not need to actively self-log her non-compliance. Jane's BAC trends over the next 2 weeks will share insights on the efficacy of the accelerant in relation to her diet-restricted weight-loss plan as well as her preference for accelerants in relation to her compliance levels. In this example, the ketone capture device reduces the need for manual data logging by the user, and also reduces the subjectivity of such data.

EXAMPLE 2

David would like to lose 30 pounds and has been using the ketone capture device for 5 days with only 10% being successful breath tests. A majority of the test failures are due to inconsistent breath pressure detected, i.e. insufficient breath sample collected. As a human analyst (or automated agent) reviews the sensor data, elevated levels of CO are logged. CO is a known breath analyte indicator for firsthand or secondhand smoking and furthermore restricts overall alveolar performance. Upon this insight, the ketone capture device parameters are adjusted from a 3 second vent/7 second sample duration to a 3 second vent/5 second sample duration. (In some embodiments, the ketone capture device may make these adjustments automatically based on measurement data it logs, or the mobile application may be capable of wirelessly programming the ketone capture device with these adjustments.) After these adjustments are made, David has been able to successfully complete his breath tests 75% of the time to monitor his weight loss progress.

EXAMPLE 3

14 months ago, Lisa began her weight loss journey with a goal to lose 50 lbs. She has been using the ketone capture device throughout numerous diet plan changes, toggling of accelerants, and intermittent pauses in her weight loss journey with external stress factors. Throughout the 14 months, her respiratory characteristics have gradually improved as displayed by a 27% to 98% successful breath test rating comparing months 1 and 14, respectively. Lisa is now 52 lbs. slimmer and her vital lung capacity and overall lung function at rest have noticeably improved as displayed by the pressure sensor readings. Improvements in her body's ability to effectively metabolize energy have been observed with positive effects on her respiratory quotient computations based on the pulse oximeter and $CO_2$ readings.

EXAMPLE 4

Brian's breath acetone levels spike and his SpO2 levels drop near the end of every month for 3 months in a row. Fluctuations of both analytes may be indicative of a high level of stress. Following this trend, there is a steady decline in his breath acetone levels coupled with steady, low SpO2 levels. After further evaluation of Brian's data early on in his program, it was reported that Brian's bills are due at the end of every month causing him to be in a high-stress state, and the following week, he rewards himself by having 1-3 alcoholic drinks in the evenings. Brian's settings are updated (by a human analyst or automated agent) to reflect both stress and alcohol as triggers to fluctuating trends in his breath acetone levels and are logged in the mobile application moving forward.

Example Uses of Temperature Monitored/Reported by Ketone Capture Device

For practical and medical applications, thermometry is performed relying heavily on probe-to-body surface contact to capture rectal, axillary, oral, and tympanic/otic temperatures, which are correlated with the core body temperature. The delta between the aforementioned temperatures and the core body temperature are dependent on the probe site and body core-to-measurement surface interface. Physiologically, the lungs are in close proximity to the core of the body and it has been clinically summarized that the deep lung temperature is representative of that of the body core. Blood circulation throughout the vascular and alveolar networks of the lungs transmits the resulting thermal energy to the exhaled alveolar breath sample. There is a temperature gradient between inhaled air and the exhaled air influenced by the fluctuating ambient temperatures, however the inhaled air is modulated by the temperature of the blood circulating from the heart's left ventricle through the bronchial arteries. Therefore, the exhaled breath temperature, hereinafter EBT, is representative of the core body temperature.

Core body temperature is physiologically one of the most tightly regulated bodily parameters. Although stringently regulated in the preoptic anterior of the hypothalamus to control thermoregulation, body temperature is known to fluctuate slightly depending on variables including but not limited to circadian rhythm, ovulation, inflammation due to ingested food or environmental allergens, hormone secretion and regulation. When the body's natural thermoregulating ability is compromised, reduced blood flow and impaired organ functionalities may occur, including but not limited to: acute renal failure, electrolyte imbalances, intravascular dehydration, cerebral ischemia, changes in normal cardiac output, metabolic acidosis. Significant changes in body temperature and EBT can be indicative of inflammation, a universal pathological response characterized by a spike in thermal energy. Body temperature is a known indicator to assess, within a couple seconds, if homeostasis is maintained at about 37 degrees C. Furthermore, EBT can be utilized as an active, actionable bioindicator of a current physiological status.

The mechanism by which sex hormones estrogen and progesterone affect thermoregulation and the responses in body temperature has not yet been clinically established. However, a biphasic pattern of high pre-menstrual and low post-menstrual temperatures can be plotted to correlate to the ovarian function and predict ovulation cycles. Impacts of estrogen include promotion of lower body temperature, heat dissipation, and vasodilation. Following the spiked secretion of estrogen towards the end of the proliferative phase, the body temperature decreases during ovulation. Post-ovulation in the secretory phase of the uterine cycle, elevated progesterone levels are manifested by an increase in temperature. At this ovarian state, the endometrium continues to thicken and the raised temperature is maintained if pregnancy occurs, otherwise returns to the homeostatic basal temperature to initiate the next menstruation cycle.

Example Uses of Resting Heart Rate Measured and Reported by Ketone Capture Device According to the National Institute of Health, the average resting heart rate, hereinafter RHR, should be 60-100 beats per minute for children 10 years and older, adults, and seniors. Well-trained and active athletes demonstrate lower average RHR of 40-60 beats per minute. Based on numerous epidemiological studies over the last three decades, there exists a significant association between RHR and all-cause and cardiovascular mortality pertaining to the general population and pre-existing cardiovascular diseases including hypertension, left ventricular dysfunction, and acute myocardial infarction. Multivariate analyses support the utility of RHR to be an independent predictor of mortality after applying respective correction factors to account for demographic and clinical parameters.

Common factors affecting heart rate include, but are not limited to: ambient environment temperatures, body position, emotional state, body size, and medication. As the temperature and humidity increase, blood flow increases and the corresponding RHR increases by 5-10 beats per minute. A bolus of neurotransmitters and hormones are secreted during events when a neutral emotional state is compromised, i.e. adrenaline is released during conditions of stress, increasing blood circulation, breathing, and carbohydrate metabolism. Medications known as beta blockers work to counteract the adrenaline and lower and maintain RHR. The thyroid hormone influences the heart rate, blood pressure, and cholesterol levels. Hypothyroidism decreases elasticity of the arteries and causes a rise in blood pressure to result in a slower heart rate. Thyroid medication, dependent on the dosage, may increase RHR. RHR is a continuous and real-time bioindicator of responses to either physiological or exogenous circumstances and the efficacy of the homeostatic regulation.

Interactants for Single-Step Reactions

As mentioned above, the disposable cartridge 32 may contain an interactant that supports a single-step chemical reaction in which no developer solution needs to be dispensed into the cartridge. Such single-step cartridges are preferably used in standalone embodiments. In single-step cartridges for measuring acetone, the interactant may include a complex including one or more metal ions and one or more primary amine molecules bound to the metal ions. The primary amine molecules may be amino acid molecules with a primary amine side chain (e.g. lysine, arginine), and the carboxylic acid group of the amino acid molecules may be bound to the metal ions. The complex including the metal ions and primary amine molecules may be further immobilized to a base material, such as silica beads. Other interactant compositions that support single-step reactions are known in the art.

Example Uses of Monitored Temperature and Pulse or Pulse Oximetry

The self-regulatory characterization of the body to maintain homeostasis persists via feedback loops between interrelated physiological systems during periods of activity and inactivity, i.e. sleep. A number of physiological variables including but not limited to glucose regulation, hormone secretion, and body temperature are controlled by sleep-dependent and circadian rhythmicity processes. Decreased body temperature during sleep is characterized by circadian rhythmicity due to the endogenous peak of melatonin, a sleep hormone produced during the evening concomitantly with the lack of light in the environment, where melatonin is comprised of hypothermic properties. The nocturnal decline of body temperature is inverse to the nocturnal rise of melatonin values. Additionally, during menstruation in the follicular phase pre-ovulation, the lowered pre-menstruation body temperature is consequential of the hypothermic response to melatonin production levels.

Another hormone relevant to sleep and the circadian rhythm is leptin, a hormone predominantly produced by adipose cells for energy expenditure regulation. There is a gradual decline in leptin production during extended periods of fasting, i.e. sleep. The decreasing leptin levels occur in concomitance with a decrease in insulin levels and increase in catecholamines. Lowered leptin levels have a critical role for physiological adaptions to starvation by decreasing metabolic rates, regardless of intake macronutrient composition, and inhibiting reproductive and thyroid functionalities.

Heart rate fluctuates by sleep stage and the efficacy of the sleep stage. In the earlier sleep stage 2, heart rate, respiration, and body temperature steadily decline through stage 3. During the final sleep stage of rapid eye movement (REM), a sustained rise in systolic blood pressure results as the body is physiologically aroused and voluntary muscles are paralyzed. Raised systolic blood pressure is evident in patients with sleep narcolepsy and obstructive sleep apnea, where pulse oximetry is a clinically used tool to monitor systolic blood pressure.

CONCLUSION

Conditional language used herein, such as, among others, "can," "might," "may," "e.g.," and the like, unless specifically stated otherwise, or otherwise understood within the context as used, is generally intended to convey that some embodiments include, while other embodiments do not include, certain features, elements, and/or states. Thus, such conditional language is not generally intended to imply that features, elements, blocks, and/or states are in any way required for one or more embodiments or that one or more embodiments necessarily include logic for deciding, with or without author input or prompting, whether these features, elements and/or states are included or are to be performed in any particular embodiment.

Although this invention has been described in terms of certain embodiments and applications, other embodiments and applications that are apparent to those of ordinary skill in the art, including embodiments which do not provide all of the features and advantages set forth herein, are also within the scope of this invention. Accordingly, the scope of the present invention is intended to be defined only by reference to the following claims

The invention claimed is:

1. A breath analysis device, comprising:
a breath input port fluidly coupled to a cartridge insertion port, said cartridge insertion port configured to receive a disposable cartridge containing an interactant, wherein the breath analysis device is configured to route at least a portion of a breath sample exhaled into the breath input port through the disposable cartridge such that an analyte in the breath sample is captured by the interactant;
a plurality of light emitting diodes (LEDs) arranged to illuminate the disposable cartridge while the disposable cartridge is inserted into the cartridge insertion port, the plurality of LEDs including at least one LED that emits light of a first wavelength and at least one LED that emits light of a second wavelength;
a photodiode positioned to receive and measure light reflected from the disposable cartridge when the disposable cartridge is illuminated; and
a processor programmed to control the plurality of LEDs during a cartridge analysis period that occurs after the breath sample is exhaled into the breath input port and while a color change occurs in the cartridge, and to receive and process measurements generated by the photodiode during the cartridge analysis period, said measurements reflective of a concentration of the analyte in the breath sample;
wherein the processor is programmed to use the LEDs and photodiode to take multiple measurements at each of the first and second LED wavelengths during the analysis period as the color change occurs in the cartridge, said measurements spaced apart in time, to thereby collect reflectance trend data at each of the first and second LED wavelengths.

2. The breath analysis device of claim 1, further comprising a light shield positioned to obstruct light emitted by the plurality of LEDs from reaching the disposable cartridge through indirect paths.

3. The breath analysis device of claim 2, wherein the light shield comprises a plurality of apertures that are arranged to enable light emitted from the LEDs to pass through the light shield and illuminate the disposable cartridge via direct light paths.

4. The breath analysis device of claim 3, wherein the light shield comprises one respective aperture for each of the plurality of LEDs.

5. The breath analysis device of claim 1, further comprising a structure that blocks light reflected from the illuminated cartridge from reaching the photodiode via an indirect path.

6. The breath analysis device of claim 1, wherein the processor is programmed to perform a plurality of measurement cycles during the cartridge analysis period, wherein, during each measurement cycle, at least the following occurs:
the disposable cartridge is illuminated with light of the first wavelength but not the second wavelength while the photodiode generates a first measurement of light reflected from the disposable cartridge; and
the disposable cartridge is illuminated with light of the second wavelength but not the first wavelength while the photodiode generates a second measurement of light reflected from the disposable cartridge.

7. The breath analysis device of claim 6, wherein the plurality of LEDs further includes at least one LED that emits light of a third wavelength, and wherein, during each measurement cycle, the cartridge is illuminated with light of the third wavelength, but not the first and second wavelengths, while the photodiode generates a third measurement of light reflected from the disposable cartridge.

8. The breath analysis device of claim 7, wherein the processor is programmed to generate an analyte concentration measurement by a process that comprises calculating ratios of photodiode measurements taken at different wavelengths.

9. The breath analysis device of claim 1, further comprising an ejection button that, when depressed, releases or expels the disposable cartridge from the cartridge insertion port.

10. The breath analysis device of claim 1, wherein each of the plurality of LEDs emits light at a wavelength falling in the range of 300 to 800 nanometers.

11. The breath analysis device of claim 1, wherein each of the plurality of LEDs emits light at a wavelength falling in the range of 350 to 740 nanometers.

12. The breath analysis device of claim 1, wherein the processor is programmed to use the multiple measurements at each of the first and second LED wavelengths in combination to generate a value representing a concentration of the analyte in the breath sample.

13. A breath analysis device, comprising:
   a breath input port fluidly coupled to a cartridge insertion port, said cartridge insertion port configured to receive a disposable cartridge containing an interactant, wherein the breath analysis device is configured to route at least a portion of a breath sample exhaled into the breath input port through the disposable cartridge such that an analyte in the breath sample is captured by the interactant;
   a plurality of light emitting diodes (LEDs) arranged to illuminate the disposable cartridge while the disposable cartridge is inserted into the cartridge insertion port, the plurality of LEDs including one or more LEDs that emit light of a first wavelength and one or more LEDs that emit light of a second wavelength; and
   a processor programmed to control the plurality of LEDs during a cartridge analysis period according to a process that comprises, during each of a plurality of measurement cycles:
      illuminating the disposable cartridge solely with the one or more LEDs that emit light of the first wavelength while generating a first measurement of light reflected from the disposable cartridge, said first measurement corresponding to the first wavelength; and
      illuminating the disposable cartridge solely with the one or more LEDs that emit light of the second wavelength while generating a second measurement of light reflected from the disposable cartridge;
   wherein the plurality of measurement cycles occur after the analyte in the breath sample is captured by the interactant and while a color change occurs in the disposable cartridge;
   wherein the first measurements taken over the plurality of measurement cycles collectively indicate a reflectance trend for the first wavelength, and the second measurements taken over the plurality of measurement cycles collectively indicate a reflectance trend for the second wavelength.

14. The breath analysis device of claim 13, wherein the plurality of LEDs further include one or more LEDs that emit light of a third wavelength, and the process further comprises, during each of the plurality of measurement cycles, illuminating the disposable cartridge solely with the one or more LEDs that emit light of the third wavelength while generating a third measurement of light reflected from the disposable cartridge, said third measurement corresponding to the third wavelength.

15. The breath analysis device of claim 14, wherein the processor is further programmed to use the first, second and third measurements taken over the plurality of measurement cycles to calculate a measurement value reflective of a concentration of the analyte captured by the interactant.

16. The breath analysis device of claim 14, wherein each of the plurality of LEDs emits light at a wavelength falling in the range of 300 to 800 nanometers.

17. The breath analysis device of claim 14, wherein each of the plurality of LEDs emits light at a wavelength falling in the range of 350 to 740 nanometers.

18. The breath analysis device of claim 13, further comprising a photodiode that generates the first and second measurements.

19. The breath analysis device of claim 13, further comprising a light shield comprising a plurality of apertures arranged to enable light from the plurality of LEDs to pass directly to the disposable cartridge, said light shield configured to block light from the LEDs from reaching the disposable cartridge via indirect paths.

20. The breath analysis device of claim 13, wherein the breath analysis device further includes an ejection button that, when depressed, releases or expels the disposable cartridge from the cartridge insertion port.

21. The breath analysis device of claim 13, further comprising program code configured to use the first measurements and the second measurements in combination to calculate a measurement value reflective of a concentration of the analyte.

* * * * *